US011428636B2

(12) United States Patent
Butte et al.

(10) Patent No.: US 11,428,636 B2
(45) Date of Patent: *Aug. 30, 2022

(54) TIME-RESOLVED LASER-INDUCED FLUORESCENCE SPECTROSCOPY SYSTEMS AND USES THEREOF

(71) Applicant: Cedars-Sinai Medical Center, Los Angeles, CA (US)

(72) Inventors: Pramod Butte, Los Angeles, CA (US); Paul Lapchak, San Diego, CA (US); David Scott Kittle, Running Springs, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/198,816

(22) Filed: Mar. 11, 2021

(65) Prior Publication Data

US 2021/0255107 A1  Aug. 19, 2021

Related U.S. Application Data

(63) Continuation of application No. 16/382,791, filed on Apr. 12, 2019, now Pat. No. 10,983,060, which is a
(Continued)

(51) Int. Cl.
*G01N 21/64* (2006.01)
*A61B 5/00* (2006.01)
(Continued)

(52) U.S. Cl.
CPC ....... *G01N 21/6486* (2013.01); *A61B 5/0071* (2013.01); *G01J 3/0218* (2013.01);
(Continued)

(58) Field of Classification Search
None
See application file for complete search history.

(56) References Cited

U.S. PATENT DOCUMENTS

| 4,097,338 A | 6/1978 | Konttinen et al. |
| 4,937,457 A | 6/1990 | Mitchell |
| (Continued) |

FOREIGN PATENT DOCUMENTS

| CN | 101262822 A | 9/2008 |
| CN | 102525481 A | 7/2012 |
| (Continued) |

OTHER PUBLICATIONS

Allen et al., Remington: The Science and Practice of Pharmacy 22nd ed., Pharmaceutical Press (Sep. 15, 2012).
(Continued)

*Primary Examiner* — David P Porta
*Assistant Examiner* — Mamadou Faye
(74) *Attorney, Agent, or Firm* — Wilson Sonsini Goodrich & Rosati

(57) ABSTRACT

The invention provides systems for characterizing a biological sample by analyzing emission of fluorescent light from the biological sample upon excitation and methods for using the same. The system includes a laser source, collection fibers, a demultiplexer and an optical delay device. All references cited herein are incorporated by reference in their entirety as though fully set forth. Unless defined otherwise, technical and scientific terms used herein have the same meaning as commonly understood by one of-ordinary skill in the art in which this invention belongs.

15 Claims, 10 Drawing Sheets

Related U.S. Application Data continuation of application No. 15/196,354, filed on Jun. 29, 2016, now Pat. No. 10,288,567, which is a continuation of application No. 14/776,086, filed as application No. PCT/US2014/030610 on Mar. 17, 2014, now Pat. No. 9,404,870.

(60) Provisional application No. 61/794,741, filed on Mar. 15, 2013.

(51) Int. Cl.
  *G01J 3/28* (2006.01)
  *G01J 3/44* (2006.01)
  *G01J 3/02* (2006.01)
  *A61B 5/1455* (2006.01)
  *A61B 5/1459* (2006.01)

(52) U.S. Cl.
  CPC ............ *G01J 3/2889* (2013.01); *G01J 3/4406* (2013.01); *G01N 21/64* (2013.01); *G01N 21/6402* (2013.01); *G01N 21/645* (2013.01); *G01N 21/6408* (2013.01); *G01N 21/6428* (2013.01); *A61B 5/0084* (2013.01); *A61B 5/1459* (2013.01); *A61B 5/14556* (2013.01); *A61B 5/4866* (2013.01); *G01N 2021/6417* (2013.01); *G01N 2021/6421* (2013.01); *G01N 2021/6484* (2013.01); *G01N 2201/06113* (2013.01)

(56) References Cited

U.S. PATENT DOCUMENTS

| | | |
|---|---|---|
| 5,196,709 A | 3/1993 | Berndt et al. |
| 5,464,013 A | 11/1995 | Lemelson |
| 5,585,089 A | 12/1996 | Queen et al. |
| 5,697,373 A | 12/1997 | Richards-Kortum et al. |
| 5,701,902 A | 12/1997 | Vari et al. |
| 5,749,830 A | 5/1998 | Kaneko et al. |
| 5,762,609 A | 6/1998 | Benaron et al. |
| 5,769,081 A | 6/1998 | Alfano et al. |
| 5,991,653 A | 11/1999 | Richards-Kortum et al. |
| 5,998,597 A | 12/1999 | Fisher et al. |
| 6,051,437 A | 4/2000 | Luo et al. |
| 6,095,982 A | 8/2000 | Richards-Kortum et al. |
| 6,097,485 A | 8/2000 | Lievan |
| 6,124,597 A | 9/2000 | Shehada et al. |
| 6,246,817 B1 | 6/2001 | Griffin |
| 6,258,576 B1 | 7/2001 | Richards-Kortum et al. |
| 6,272,376 B1 | 8/2001 | Marcu et al. |
| 6,427,082 B1 | 7/2002 | Nordstrom et al. |
| 6,571,118 B1 | 5/2003 | Utzinger et al. |
| 6,697,652 B2 | 2/2004 | Georgakoudi et al. |
| 6,697,666 B1 | 2/2004 | Richards-Kortum et al. |
| 6,912,412 B2 | 6/2005 | Georgakoudi et al. |
| 6,933,154 B2 | 8/2005 | Schomacker et al. |
| 6,975,899 B2 | 12/2005 | Faupel et al. |
| 7,015,484 B2 | 3/2006 | Gillispie et al. |
| 7,103,401 B2 | 9/2006 | Schomacker et al. |
| 7,113,814 B2 | 9/2006 | Ward et al. |
| 7,127,282 B2 | 10/2006 | Nordstrom et al. |
| 7,136,518 B2 | 11/2006 | Griffin et al. |
| 7,192,783 B2 | 3/2007 | Alfano et al. |
| 7,253,894 B2 | 8/2007 | Zeng et al. |
| 7,260,248 B2 | 8/2007 | Kaufman et al. |
| 7,515,952 B2 | 4/2009 | Balas et al. |
| 7,647,092 B2 | 1/2010 | Motz et al. |
| 7,890,157 B2 | 2/2011 | Jo et al. |
| 8,005,527 B2 | 8/2011 | Zelenchuk |
| 8,049,880 B2 | 11/2011 | Robbins et al. |
| 8,089,625 B2 | 1/2012 | Marcu et al. |
| 8,380,268 B2 | 2/2013 | Georgakoudi et al. |
| 8,405,827 B2 | 3/2013 | Claps |
| 9,404,870 B2 | 8/2016 | Butte et al. |
| 10,288,567 B2 | 5/2019 | Butte et al. |
| 10,656,089 B2 | 5/2020 | Butte et al. |
| 10,983,060 B2 * | 4/2021 | Butte ................. G01N 21/6486 |
| 2002/0016533 A1 | 2/2002 | Marchitto et al. |
| 2002/0197736 A1 | 12/2002 | Amirkhanian |
| 2003/0136921 A1 | 7/2003 | Reel |
| 2003/0236458 A1 | 12/2003 | Hochman |
| 2004/0029213 A1 | 2/2004 | Callahan et al. |
| 2004/0039269 A1 | 2/2004 | Ward et al. |
| 2004/0043502 A1 | 3/2004 | Song et al. |
| 2004/0225222 A1 | 11/2004 | Zeng et al. |
| 2005/0105791 A1 | 5/2005 | Lee et al. |
| 2006/0058683 A1 | 3/2006 | Chance |
| 2006/0197033 A1 | 9/2006 | Hairston et al. |
| 2006/0223172 A1 | 10/2006 | Bedingham et al. |
| 2006/0229515 A1 | 10/2006 | Sharareh et al. |
| 2007/0194249 A1 | 8/2007 | Gavrilov et al. |
| 2007/0197894 A1 | 8/2007 | Jo et al. |
| 2008/0068615 A1 | 3/2008 | Striemer et al. |
| 2008/0171383 A1 | 7/2008 | Selker et al. |
| 2009/0095911 A1 | 4/2009 | Kim et al. |
| 2009/0099460 A1 | 4/2009 | Zuluaga |
| 2010/0067003 A1 | 3/2010 | Marcu et al. |
| 2010/0069720 A1 | 3/2010 | Fulghum et al. |
| 2010/0106025 A1 | 4/2010 | Sarfaty et al. |
| 2010/0198080 A1 | 8/2010 | Liu et al. |
| 2010/0231896 A1 | 9/2010 | Mann et al. |
| 2010/0234684 A1 | 9/2010 | Blume et al. |
| 2011/0311442 A1 | 12/2011 | Ehringer et al. |
| 2011/0319759 A1 | 12/2011 | Liu et al. |
| 2012/0010541 A1 | 1/2012 | Cain et al. |
| 2012/0035442 A1 | 2/2012 | Barman et al. |
| 2012/0088262 A1 | 4/2012 | Dehghani et al. |
| 2012/0245473 A1 | 9/2012 | Mycek et al. |
| 2013/0076861 A1 | 3/2013 | Sternklar |
| 2013/0087718 A1 | 4/2013 | Mei et al. |
| 2013/0218479 A1 | 8/2013 | Claps |
| 2014/0187879 A1 | 7/2014 | Wood et al. |
| 2015/0320319 A1 | 11/2015 | Alfano et al. |
| 2016/0003742 A1 | 1/2016 | Butte et al. |
| 2016/0374562 A1 | 12/2016 | Vertikov |
| 2017/0290515 A1 | 10/2017 | Butte et al. |
| 2020/0319108 A1 | 10/2020 | Butte et al. |

FOREIGN PATENT DOCUMENTS

| | | |
|---|---|---|
| CN | 102770071 A | 11/2012 |
| CN | 105359028 A | 2/2016 |
| EP | 0442295 A2 | 8/1991 |
| EP | 1287114 A2 | 3/2003 |
| JP | H07222712 A | 8/1995 |
| JP | H07229835 A | 8/1995 |
| JP | H09121892 A | 5/1997 |
| JP | 2001509589 A | 7/2001 |
| JP | 2004305382 A | 11/2004 |
| JP | 2005512086 A | 4/2005 |
| JP | 2007501414 A | 1/2007 |
| JP | 2008511824 A | 4/2008 |
| JP | 2011503552 A | 1/2011 |
| JP | 2011062348 A | 3/2011 |
| JP | 2011196852 A | 10/2011 |
| JP | 2013027392 A | 2/2013 |
| WO | WO-9006718 A1 | 6/1990 |
| WO | WO-9009637 A1 | 8/1990 |
| WO | WO-9510766 A1 | 4/1995 |
| WO | WO-0008443 A1 | 2/2000 |
| WO | WO-0194528 A2 | 12/2001 |
| WO | WO-2005019800 A2 | 3/2005 |
| WO | WO-2006086382 A2 | 8/2006 |
| WO | WO-2013131062 A1 | 9/2013 |
| WO | WO-2014145786 A1 | 9/2014 |
| WO | WO-2014168734 A1 | 10/2014 |
| WO | WO-2017075176 A1 | 5/2017 |
| WO | WO-2017173315 A1 | 10/2017 |
| WO | WO-2017177194 A1 | 10/2017 |

(56) References Cited

OTHER PUBLICATIONS

Bigio et al. Ultraviolet and visible spectroscopies for tissue diagnostics: fluorescence spectroscopy and elastic-scattering spectroscopy. Physics in Medicine and Biology (1997). 42(5):803-814.
Blackwell et al. In vivo time-resolved autofluorescence measurements to test for glycation of human skin. Journal of Biomedical Optics (2008). 13(1): 014004.
Butte, et al. 2005. Diagnosis of meningioma by time-resolved fluorescence spectroscopy. Journal of Biomedical Optics, 10(6), 064026. doi:10.1117/1.2141624.
Butte, et al. 2010. Fluorescence lifetime spectroscopy for guided therapy of brain tumors. NeuroImage, 54, S125-S135. doi:10.1016/j.neuroimage.2010.11.001.
Butte, et al. 2010. Intraoperative delineation of primary brain tumors using time-resolved fluorescence spectroscopy. Journal of Biomedical Optics, 15(2), 027008. doi:10.1117/1.3374049.
Butte, P. et al. Time-Resolved Laser Induced Fluorescence Spectroscopy (TRLIFS): A Tool for Intra-operative Diagnosis of Brain Tumors and Maximizing Extent of Surgical Resection. Tumors of the Central Nervous System, vol. 5 (2012), pp. 161-172.
Co-pending U.S. Appl. No. 16/100,638, inventors Blackkeith; L. et al., filed Aug. 10, 2018.
Co-pending U.S. Appl. No. 17/578,932, inventors Butte; Pramod et al., filed Jan. 19, 2022.
EP16860766.1 European Search Report dated Mar. 6, 2018.
EP17186617.1 European Search Report dated Feb. 7, 2018.
EP17776805.8 Extended European Search Report dated Nov. 8, 2019.
European search report with written opinion dated Dec. 12, 2016 for EP14763125.
Examination Report dated Aug. 3, 2010 European patent application No. 04781453.8 (filed Aug. 19, 2004), 4 pages.
Examination Report dated Dec. 15, 2008 for European patent application No. 04781453.8 (filed Aug. 19, 2004), 4 pages.
Examination Report dated Sep. 11, 2009 European patent application No. 04781453.8 (filed Aug. 19, 2004), 2 pages.
Examination Report dated Feb. 25, 2009 for Japanese patent application No. 2006-523995 (filed Aug. 19, 2004), 7 pages.
Examination Report dated Feb. 8, 2010 for Japanese patent application No. 2006-523995 (filed Aug. 19, 2004), 4 pages.
Fang et al., "Time-Domain laser-Induced Fluorescence Spectroscopy Apparatus for Clinical Diagnostics," Rev. Sci. Instrum., vol. 75, No. 1, pp. 151-162 (2004).
Gallagher NB, et al.,Curve resolution for multivariate images with applications to TOF-SIMS and Raman. Chemometrics and Intelligent Laboratory Systems 2004, 73(1): 105-117.
Greenfield, Antibodies A Laboratory Manual 2nd ed., Cold Spring Harbor Press (Cold Spring Harbor N.Y., 2013).
Haaland, DM., et al., Hyperspectral Confocal Fluorescence Imaging: Exploring Alternative Multivariate Curve Resolution Approaches. Appl Spectrosc 2009, 63(3):271-279.
Haaland, et al., "New augmented classical least squares methods for improved quantitative spectral analyses." Vibrational Spectroscopy 29.1 (2002): 171-175.
Haaland, et al., "New prediction-augmented classical least-squares (PACLS) methods: application to unmodeled interferents." Applied Spectroscopy 54.9 (2000): 1303-1312.
Hornyak et al., Introduction to Nanoscience and Nanotechnology, CRC Press (2008).
Huang et al. Laser-induced autofluorescence microscopy of normal and tumor human colonic tissue. Int J Oncol (2004). 24(1):59-63.
International Preliminary Report on Patentability dated Sep. 24, 2015 for International Application No. PCT/US2014/029781 (7 pages).
International Preliminary Report on Patentability dated Sep. 24, 2015 for International Application No. PCT/US2014/030610 (7 pages).
International Preliminary Report on Patentability dated Feb. 21, 2006 for PCT patent application No. PCT/US04/26759 (filed Aug. 19, 2004), 6 pages.
International Search Report and Written Opinion dated Aug. 10, 2017 for International PCT Patent Application No. PCT/US2017/026697.
International Search Report dated Jul. 25, 2014 for International Application No. PCT/US2014/029781 (3 pages).
International Search Report dated Jul. 30, 2014 for International Application No. PCT/US2014/030610 (3 pages).
International search report with written opinion dated Feb. 27, 2017 for PCT/US2016/059054.
International search report with written opinion dated Jun. 16, 2017 for PCT/US2017/025451.
International search report with written opinion dated Nov. 14, 2005 for PCT/US2004/026759.
Jermyn et al., Intraoperative brain cancer detection with Raman spectroscopy in humans, Science Translational Medicine, Feb. 11, 2015, 7(274) 274ra19 (9 pages).
Jo et al., "Fast Model-Free De-convolution of Fluorescence Decay for Analysis of Biological Systems," J. Biomed. Opt., vol. 9, No. 4., pp. 743-752 (2004).
Jo et al., "Laguerre Nonparametric De-convolution Technique of Time-Resolved Fluorescence Data; Application to the Prediction of Concentrations in a Mixture of Biochemical Components" Conference; Jul. 21, 2004; Proc. SPIE, vol. 5326, Jul. 21, 2004.
Jo et al., "Nonparametric Analysis of Time-Resolved Fluorescence Data Based on the Laguerre Expansion Technique" Proceedings of the 25th Annual International Conference of the IEEE Engineering in Medicine and biology Society, Sep. 17, 2003; pp. 1015-1018; vol. 2.
Kohler et al. Derivation of specific antibody-producing tissue culture and tumor lines by cell fusion. European Journal of Immunology, 6.7 (1976): 511-519.
Kut et al., Detection of Human Brain Cancer Infiltration ex vivo and in vivo Using Quantitative Optical Coherence Tomography, Sci Transl Med., Jun. 17, 2015; 7(292): 292ra100.
Lakowicz, J. R. (2006). Principles of fluorescence spectroscopy (3rd ed., p. xxvi, 954 p.). New York: Springer. Retrieved from http://www.loc.gov/catdir/enhancements/fy0824/2006920796-b.html.
Ma et al., Technique for real-time tissue characterization based on scanning multispectral fluorescence lifetime spectroscopy (ms-TRFS), 2015, Optics Express vol. 6, No. 3, pp. 987-1002.
Maarek et al., Time-resolved Fluorescence Spectra of Arterial Fluorescent Compounds: Reconstruction with the Laguerre Expansion Technique, 2000, Photochemistry and Photobiology, 71(2), 178-187.
Marcu, et al. (2004). Fluorescence lifetime spectroscopy of glioblastoma multiforme. Photochemistry and Photobiology, 80, 98-103. doi:10.1562/2003-12-09-RA-023.1.
Marcu, L. Fluorescence lifetime in cardiovascular diagnostics. J Biomed Opt. Jan.-Feb. 2010;15(1):011106. doi: 10.1117/1.3327279.
Mayinger et al. Evaluation of in vivo endoscopic autofluorescence spectroscopy in gastric cancer. Gastrointest Endosc (2004). 59(2):191-198.
Notice of allowance dated Apr. 4, 2016 for U.S. Appl. No. 14/776,086.
Notice of Allowance dated Nov. 15, 2010 for U.S. Appl. No. 10/567,248.
Notice of Allowance dated Dec. 23, 2020 for U.S. Appl. No. 16/382,791.
Office action dated Feb. 3, 2017 for U.S. Appl. No. 15/196,354.
Office action dated May 9, 2017 for U.S. Appl. No. 15/475,750.
Office action dated Aug. 24, 2010 for U.S. Appl. No. 10/567,248.
Office Action dated Aug. 28, 2017 for U.S. Appl. No. 15/475,750.
Office Action dated Sep. 5, 2017 for U.S. Appl. No. 15/196,354.
Office action dated Sep. 11, 2009 for U.S. Appl. No. 10/567,248.
Office Action dated Sep. 14, 2017 for U.S. Appl. No. 15/482,442.
Office action dated Dec. 1, 2020 for U.S. Appl. No. 16/849,102.
Office Action dated Dec. 10, 2015 for U.S. Appl. No. 14/776,086.
Phipps, J.E. Time-resolved fluorescence techniques for atherosclerotic cardiovascular disease characterization. 2005, a Ph.D. Dissertation, University of California, Davis. 119 pages. (Year: 2005).

(56) References Cited

OTHER PUBLICATIONS

Pogue, et al. (2001). In vivo NADH fluorescence monitoring as an assay for cellular damage in photodynamic therapy. Photochemistry and Photobiology, 74(6), 817-24. Retrieved from http://www.ncbi.nlm.nih.gov/pubmed/11783938.
Riechmann et al. Reshaping human antibodies for therapy. Nature, 332.6162:323-7 (1988).
Rolinsky et al. (2001) A New Approach to Fluorescence Lifetime Sending Based on Molecular Distributions. Proceedings of SPIE, vol. 4252, pp. 1-11.
Sambrook, et al. Molecular Cloning: A Laboratory Manual. 4th Edition, 2012.
Schneckenburger, H. (1992). Fluorescence decay kinetics and imaging of NAD(P)H and flavins as metabolic indicators. Optical Engineering, 31(7), 1447. doi:10.1117/12.57704.
Search Report dated Sep. 25, 2008 for European patent application No. 04781453.8 (filed Aug. 19, 2004), 5 pages.
Siegel et al, "Studying Biological Tissue with Fluorescence Lifetime Imaging; Microscopy, Endoscopy, and Decay Profiles," Applied Optics, vol. 42 pp. 2995-3004 (2003).
Singleton, Dictionary of DNA and Genome Technology 3rd ed., Wiley-Blackwell (Nov. 28, 2012).
Singleton, Dictionary of Microbiology and Molecular Biology 3.sup.rd ed., revised ed., J. Wiley & Sons (New York, N.Y. 2006).
Smith, March's Advanced Organic Chemistry Reactions, Mechanisms and Structure 7.sup.th ed., J. Wiley & Sons (New York, N.Y. 2013).
Sun et al. Simultaneous time-and wavelength-resolved fluorescence spectroscopy for near real-time tissue diagnosis. Optics Letters (2008). 33(6):630-632.
Sun, Y., et al. (2009). Fluorescence lifetime imaging microscopy: in vivo application to diagnosis of oral carcinoma. Opt Lett, 34(13), 2081-2083. doi:183277.
Thomas, et al., Comparison of multivariate calibration methods for quantitative spectral analysis. Analytical Chemistry 1990 62 (10), 1091-1099.
Thomas, E.V., A primer on multivariate calibration. Analytical Chemistry 1994 66 (15), 795A-804A.
U.S. Appl. No. 15/196,354 Notice of Allowance dated Jan. 11, 2019.
U.S. Appl. No. 15/196,354 Office Action dated Jun. 6, 2018.
U.S. Appl. No. 15/475,750 Notice of Allowance dated Mar. 5, 2020.
U.S. Appl. No. 15/475,750 Office Action dated Apr. 8, 2019.
U.S. Appl. No. 15/475,750 Office Action dated Mar. 5, 2018.
U.S. Appl. No. 15/475,750 Office Action dated Oct. 11, 2018.
U.S. Appl. No. 15/475,750 Office Action dated Oct. 24, 2019.
U.S. Appl. No. 15/482,442 Office Action dated Apr. 16, 2018.
U.S. Appl. No. 16/382,791 Office Action dated May 5, 2020.
U.S. Appl. No. 16/849,102 Office Action dated May 7, 2021.
Wilson, et al. An optical fiber-based diffuse reflectance spectrometer for non-invasive investigation of photodynamic sensitizers in vivo. Proc. SPIE 6, 219-232, Jan. 21, 1990.
Written Opinion dated Jul. 25, 2014 International Application No. PCT/US2014/029781 (5 pages).
Written Opinion dated Jul. 30, 2014 for International Application No. PCT/US2014/030610 (5 pages).
Written Opinion dated Nov. 14, 2005 for PCT patent application No. PCT/US04/26759 (filed Aug. 19, 2004), 5 pages.
Yankelevich et al. Design and evaluation of a device for fast multispectral time-resolved fluorescence spectroscopy and imaging. Rev Sci Instrum. Mar. 2014;85(3):034303.
Yong, et al. Distinction of brain tissue, low grade and high grade glioma with time-resolved fluorescence spectroscopy. Front Biosci. May 1, 2006;11:1255-1263. doi: 10.2741/1878.
U.S. Appl. No. 16/849,102 Notice of Allowance dated Oct. 22, 2021.
U.S. Appl. No. 16/849,102 Office Action dated Feb. 7, 2022.

* cited by examiner

TIME-RESOLVED LASER-INDUCED FLUORESCENCE SPECTROSCOPY SYSTEMS AND USES THEREOF

CROSS-REFERENCE

This application is a continuation of U.S. patent application Ser. No. 16/382,791, filed Apr. 12, 2019, which is a continuation of U.S. patent application Ser. No. 15/196,354, filed Jun. 29, 2016, now U.S. Pat. No. 10,288,567, which is a continuation of U.S. patent application Ser. No. 14/776,086, filed Sep. 14, 2015, now U.S. Pat. No. 9,404,870, which is a national stage application of International Application No. PCT/US2014/030610, filed Mar. 17, 2014, which claims the benefit of U.S. Provisional Application No. 61/794,741, filed Mar. 15, 2013; which are incorporated herein by reference for all purposes in their entireties.

STATEMENT AS TO FEDERALLY SPONSORED RESEARCH

This invention was made with government support under Grant No. NS060685 awarded by the National Institutes of Health. The government has certain rights in the invention.

FIELD OF INVENTION

The present invention relates generally to techniques for characterizing biological materials by analyzing laser-induced light emissions from labeled or unlabeled biomolecules.

BACKGROUND OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2n$^{d}$ ed, Cold Spring Harbor Press (Cold Spring Harbor N.Y., 2013); Kohler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

Laser-induced fluorescence spectroscopy (LIFS) has been extensively applied to complex biological systems to diagnose diseases, such as tumors or atherosclerotic plaques, and to analyze chemical or biochemical composition of organic matters. The benefit of LIFS includes its noninvasive approach to obtain both qualitative and quantitative information of a biological system in vivo. Additional advantages of LIFS include wavelength tunability, narrow bandwidth excitation, directivity and short pulses excitation. Furthermore, LIFS can selectively and efficiently excite the fluorophores in organic matter and greatly improve the fluorescence selectivity and detectability.

Time-resolved techniques allow real-time evolution of the laser-induced emission to be directly recorded which was made possible by the availability of short (nanoseconds) and ultra-short (picoseconds) pulsed lasers, as well as advances in high-speed electronics. Because the light emission process occurs in a very short time interval after the stimulating event (e.g., fluorescence decay time is in the order of nanoseconds), the time-resolved measurement can provide information about molecular species and protein structures of the sample. For example, the time-resolved techniques permit "early" processes (typically the direct excitation of short-lived states or very rapid subsequent reactions) and "late" processes (typically from long-lived states, delayed excitation by persisting electron populations or by reactions which follow the original electron process) to be "separated" in the measured data.

The time-resolved measurement only obtains an integrated effect from a wide range of wavelengths and can be complemented by spectral information in the laser-induced emission to reveal additional characteristics of a sample. To resolve the laser-induced emission into component wavelengths while still being able to perform time-resolved measurement, some existing LIFS techniques use a scanning monochromator to select wavelengths from the broadband emission one wavelength at a time, and to direct the selected wavelength component to the photodetector. However, to resolve another wavelength from the emission spectrum, the sample has to be excited again to produce another reemission, while the monochromator is tuned to select the new wavelength.

These existing techniques can take a significant amount of time to resolve multiple spectral components from a wide band light emission. Although each wavelength component can be recorded in real-time, the transition time of using a monochromator to select another wavelength can take up to a few seconds, which becomes the limiting factor in performing real-time measurements. Furthermore, an overall measurement can take a large amount of time if a large number of stimulation locations on the sample have to be measured. Hence, there is a need for systems and methods that facilitates near real-time recording of both time-resolved and wavelength-resolved information from a light emission caused by a single excitation of a sample.

SUMMARY OF THE INVENTION

The invention provides a system that characterizes a biological sample by analyzing light emissions from the biological sample in response to an excitation signal. The system first radiates the biological sample with a laser impulse to cause the biological sample to produce a responsive light emission. The system then uses a wavelength-splitting device to split the responsive light emission into a set of spectral bands of different central wavelengths. Temporal delays are then applied to the set of spectral bands so that each spectral band arrives at an optical detector at a different time, thereby allowing the optical detector to temporally resolve the responsive light emission for each spectral band separately. The delayed spectral bands are then captured by the system within a single detection window of the optical detector. The captured spectral bands are subsequently processed.

BRIEF DESCRIPTION OF FIGURES

In accordance with various embodiments of the present invention.

In accordance with various embodiments of the present invention.

DETAILED DESCRIPTION OF THE INVENTION

Figure 1A:
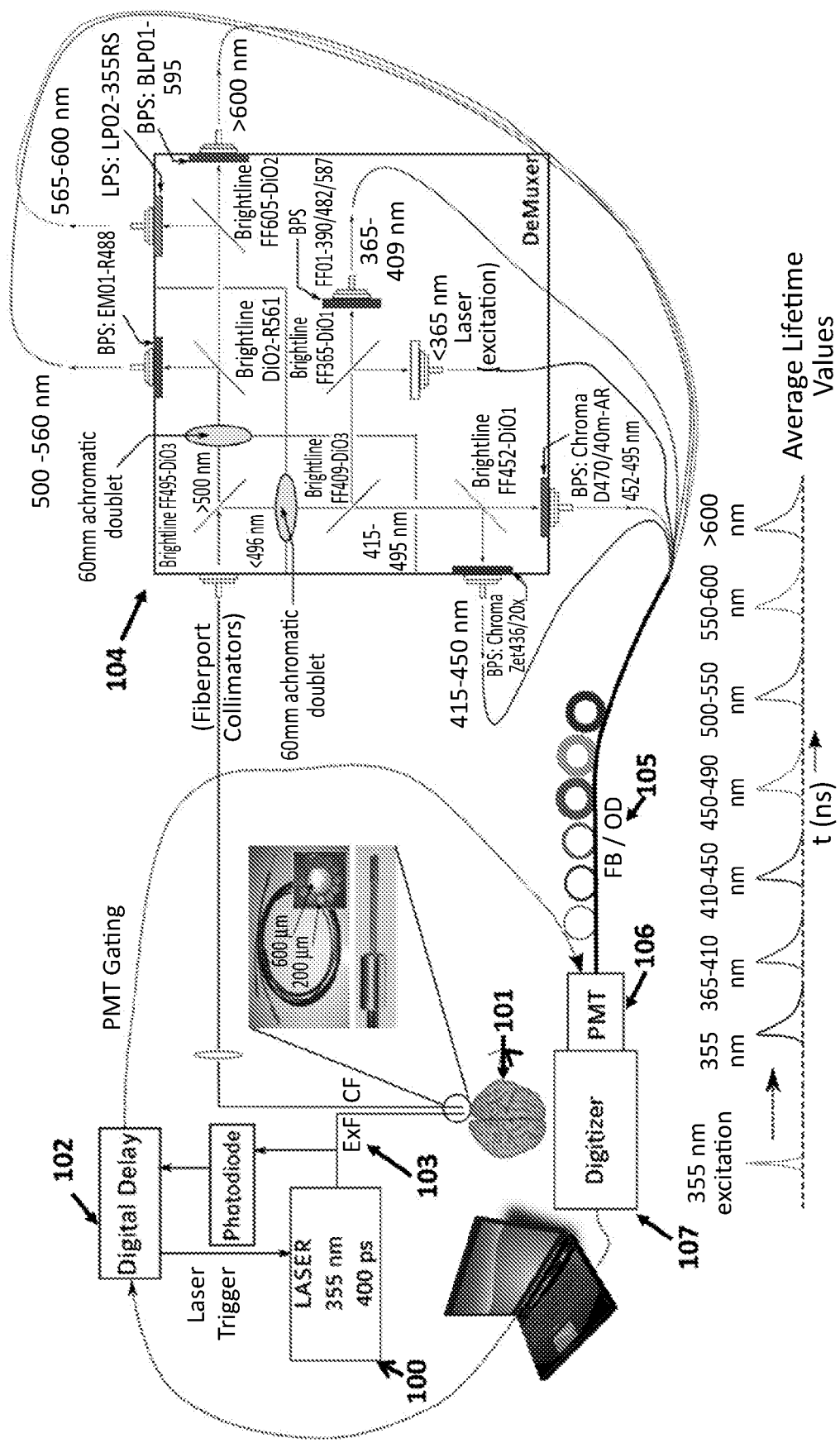
FIG. 1A depicts, in accordance with various embodiments of the present invention, a schematic of multi-excitation time-resolved laser-induced fluorescence spectroscopy. BS: beam splitter; FB: fiber bundle; OD: optical density; LPFW: long pass filter wheel; ExF: excitation fiber; CF: collection fiber; PMT: photo multiplier tube.

All references cited herein are incorporated by reference in their entirety as though fully set forth. Unless defined otherwise, technical and scientific terms used herein have the same meaning as commonly understood by one of ordinary skill in the art to which this invention belongs. Allen el al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Kohler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The present invention relates to techniques for characterizing biological materials by analyzing laser-induced light emissions from biomolecules (labeled or unlabeled). More specifically, the present invention relates to a method and apparatus for characterizing biological materials by performing a time-resolved and wavelength-resolved analysis on laser-induced fluorescence emissions from the biological materials.

The system described herein may be used for characterizing various physiological and disease states, including but not limited to assessing post-injury tissue viability, tumor and tumor-margin detection, continuous monitoring of cellular metabolism, monitoring blood plasma to optimize drug therapies. The system can be adapted to various applications/uses, depending on the substrate/marker being assayed.

The System

The excitation source is a pulsed laser 100. Output pulses from pulsed laser radiate upon a biological sample at a predetermined wavelength and power level that is suitable for exciting biological sample 101 without causing damage to the sample. Pulse laser is controlled by an internal or external pulse controller device or a digital delay device or a trigger device 102, which provides precise timing to each laser impulse output. This precise timing is checked at every pulse using a photodiode and updated using an analog to digital converter device e.g. NI PCIe-6220. In one embodiment, pulsed laser emits ultraviolet (UV) light pulses to excite biological sample. In another embodiment, pulsed laser emits visible or near infra-red light pulses to excite biological sample.

The laser emission from pulsed laser can be coupled/focused into an optical fiber, and guided to a specific location on biological sample through either the optical fiber 103 (FIG. 3) or a lens system. Laser-impulse excitation causes biological sample to produce a responsive light emission, such as a fluorescence emission, which typically has a wide spectrum comprising many wavelengths. This laser-induced light emission is then collected by one or more light-collecting fibers or lenses. In one embodiment of the present invention, light-collecting fiber is a bundle of multi-mode fibers 103. In another embodiment the light collecting is achieved using a objective lens.

Light-collecting fiber then brings the wide band emission light into a wavelength-splitting device 104 (FIG. 2), which can comprise one or more wavelength-splitting stages. The wide band emission light undergoes a series of wavelength splitting processes so that the wide band signal can be resolved into a number of narrow spectral bands, each with a distinct central wavelength. The wavelength-resolved spectral bands are coupled into a corresponding delay device 105, which applies a predetermined temporal delay to each spectral band as it travels towards a photodetector 106. The temporally-delayed spectral bands exiting the delay device are arranged onto a fast-response photomultiplier tube so that the fluorescence decay profile of each wavelength-resolved spectral band including the laser light can be individually recorded and temporally resolved. The delays applied to these spectral bands allow each optical signal to arrive at the multi-channel plate photomultiplier tube (MCP-PMT) at a different time, which allows the decay profile of each spectral band detected by the MCP-PMT separately, along with the laser light. In one embodiment, the output from MCP-PMT can be recorded and displayed using a high-speed digitizer 107. In another embodiment, the output from MCP-PMT can be recorded and displayed using an oscilloscope. In an embodiment, MCP-PMT is a gated, MCP-PMT controlled by a gate control circuit, so that MCP-PMT only responds to light signals during a narrow detection window when MCP-PMT is open. In one embodiment, gate control circuit and pulse control are synchronized so that all the fluorescence decay profiles associated with a single laser-induced excitation may be recorded within a single MCP-PMT detection window. In an embodiment, the timing of the MCP-PMT gate opening is synchronized to the laser pulse by changing the delay between the laser trigger and MCP-PMT gate using a correction based on the previous delay. The trigger delay in the laser (the delay between the trigger signal and actual firing of laser light) is recorded using a photodiode. The measured trigger delay is used to correct the synchronization between the laser triggering and MCP-PMT gate. Other photodetectors including but not limited to avalanche photodiodes (APDs), silicon PMT, may be used instead of or in addition to MCP-PMTs. The gain of the MCP-PMT can be controlled automatically. In one embodiment of the present invention the MCP-PMT voltage can be dynamically changed based on the fluorescence signal. In one embodiment of the present invention the voltage change is determined by analyzing the fluorescence signal and determining the amount of change prior to recording the signal.

Figure 1B:
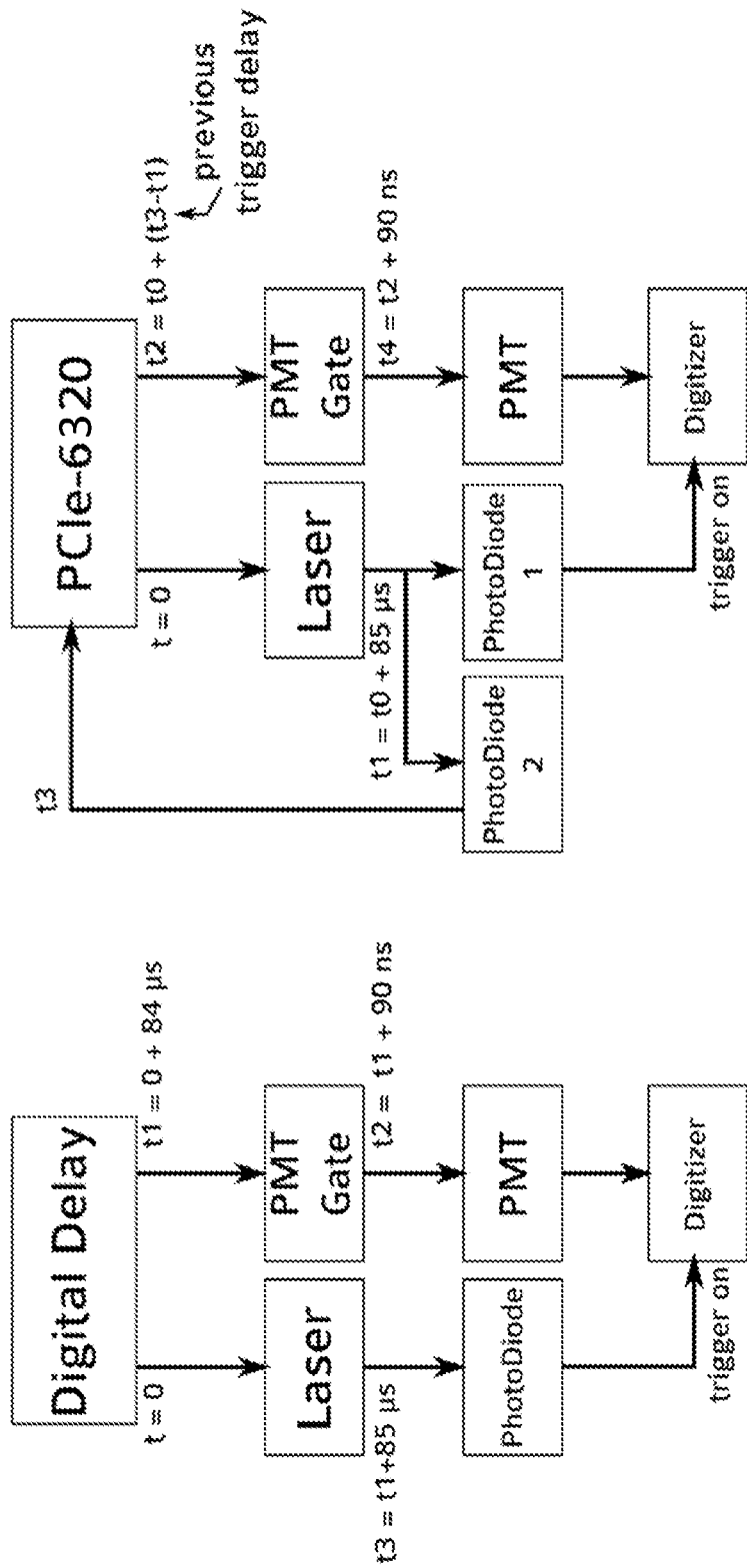
FIG. 1B shows trigger synchronization.

The pulsed laser 103 has an inherent delay generating laser light after the unit has been externally triggered. In an exemplary embodiment, the delay in generating the laser light after external delay can be up to but not limited to 85 microseconds. The delay in triggering the signal henceforth referred to as 'trigger delay' can vary between each pulse of laser. In order to synchronize the laser light with the PMT gating, the inventors use a photodiode to detect the timing of the laser pulse and compare it to the external trigger and then correct the timing of next trigger based on the last trigger delay (FIG. 1B). In FIG. 1B, t0 is when the laser is triggered, t1 is when the laser fires, t2 is when the PMT is triggered and t3 is when the PMT gate turns on. By enabling this feedback based trigger synchronization t2 is dynamically set to ensure that the voltage gain on the MCP-PMT is 'on' when the fluorescent signal reaches the MCP-PMT. The digitizer is triggered 'on' using a second photodiode to ensure smaller data size.

A schematic diagram of the TRLIFS system is depicted in FIG. 1. In various embodiments, the system comprises: (i) excitation fibers (ExF), (ii) collection fibers (CF), (iii) a demultiplexer (demuxer), a wavelength splitting device that provides micro-measurements about the lifetime of the fluorescence signal, (i.e. the exponential decay of the fluorescence signal), (iv) a photomultiplier tube (MCP-PMT, for example, a high gain ($10^6$), low noise and fast rise time detector (~80 ps) such as Photek 210), (v) an optional preamplifier to provide additional gain after photomultiplier tube before the signal is digitized, (vi) a digitizer to digitizes the signal received from the Photomultiplier Tube (for example at 6.4 G samples/second), in order to perform data analysis (for example, SP Devices: 108ADQ Tiger), and (vii) a computer system to process and display the signal.

The fluorescence signal from the biological tissue can be very high or low based on the fluorophore in the biological system. The fluorophore emits fluorescence emission intensity based on the quantum efficiency and/or absorption of excitation light which may be blocked due to certain conditions such as the type of sample (for example, tissue, blood, plasma). In order to properly record the fluorescence spectra, the PMT gain needs to be adjusted such that the increased fluorescence emission does not cause saturation of the signal and low fluorescence emission does not lead to very low signal to noise ratio. This can be achieved by rapidly changing the voltage across the MCP-PMT based on the previously recorded data. In one embodiment, fluorescence light from two pulses of laser is averaged and analyzed (for example, using software) to determine whether the fluorescence signal is too high or too low, after which the voltage across the MCP-PMT (responsible for controlling the gain of PMT) is changed via communicating between the high voltage power supply and the computer. In case the fluorescence emission is too high the voltage is reduced and vice a versa iteratively till the correct amount of signal to noise ratio is achieved. The true signal is saved and analyzed only after the correct SNR is achieved.

Figure 3:
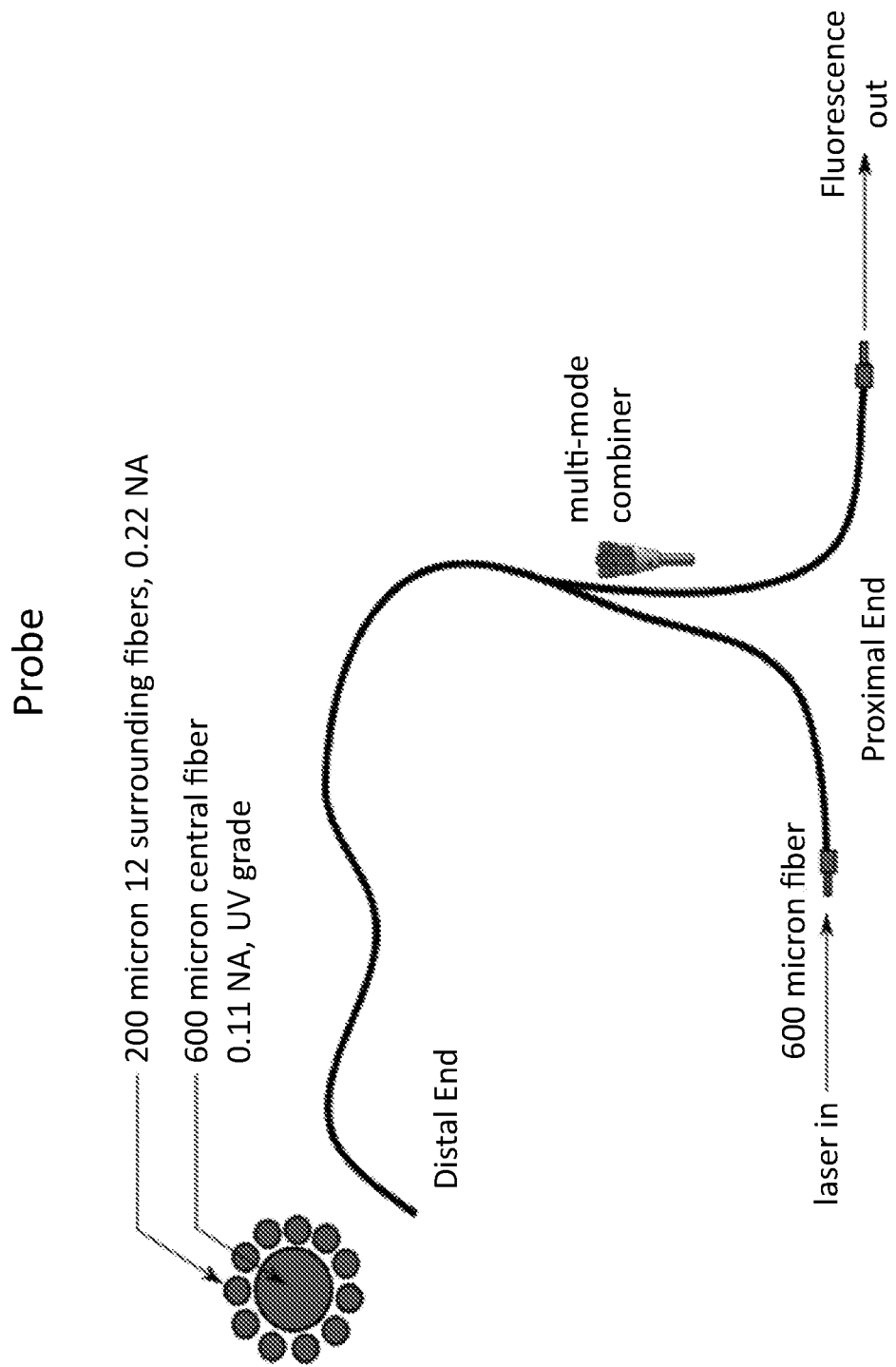
FIG. 3 depicts, in accordance with various embodiments of the present invention, a schematic of the probe.

In some embodiments, the excitation fiber (for example, a 600 μm diameter with 0.12 NA, UV grade silica core fiber) connects the laser source to the sample so as to excite the sample at a desired wavelength. The collection fibers (for example 12 fibers of 200 μm diameter with 0.22 NA, UV grade silica core fiber) are packaged into a single bundle; this bundle leads to the demultiplexer (FIG. 3). The 12 fibers can be combined into a single fiber using a technique of combining multi-mode fibers in a single fiber. (http://www.ofsoptics.com/). Upon excitation of the sample with a laser at a pre-determined wavelength, the collection fibers collect the fluorescence signal from the sample, and relay the signal to the demultiplexer. Various wavelength-splitting filters in the demultiplexer split the incoming signal based on the wavelengths of the beam splitting devices such as but not limited to filters or prisms etc. The fluorescence signal pulse (after pulsed excitation) is relayed to the computer system via the photomultiplier tube, the preamplifier and the digitizer, where the fluorescence decay is calculated by deconvolving the (previously recorded) laser pulse from the recorded fluorescence pulse.

In various embodiments, the sample is any one or more of blood, plasma, tissue, micriorganisms, parasites, sputum or any other biological sample from which the chemical signature can be detected.

Wavelength Splitting Device

Figure 2:
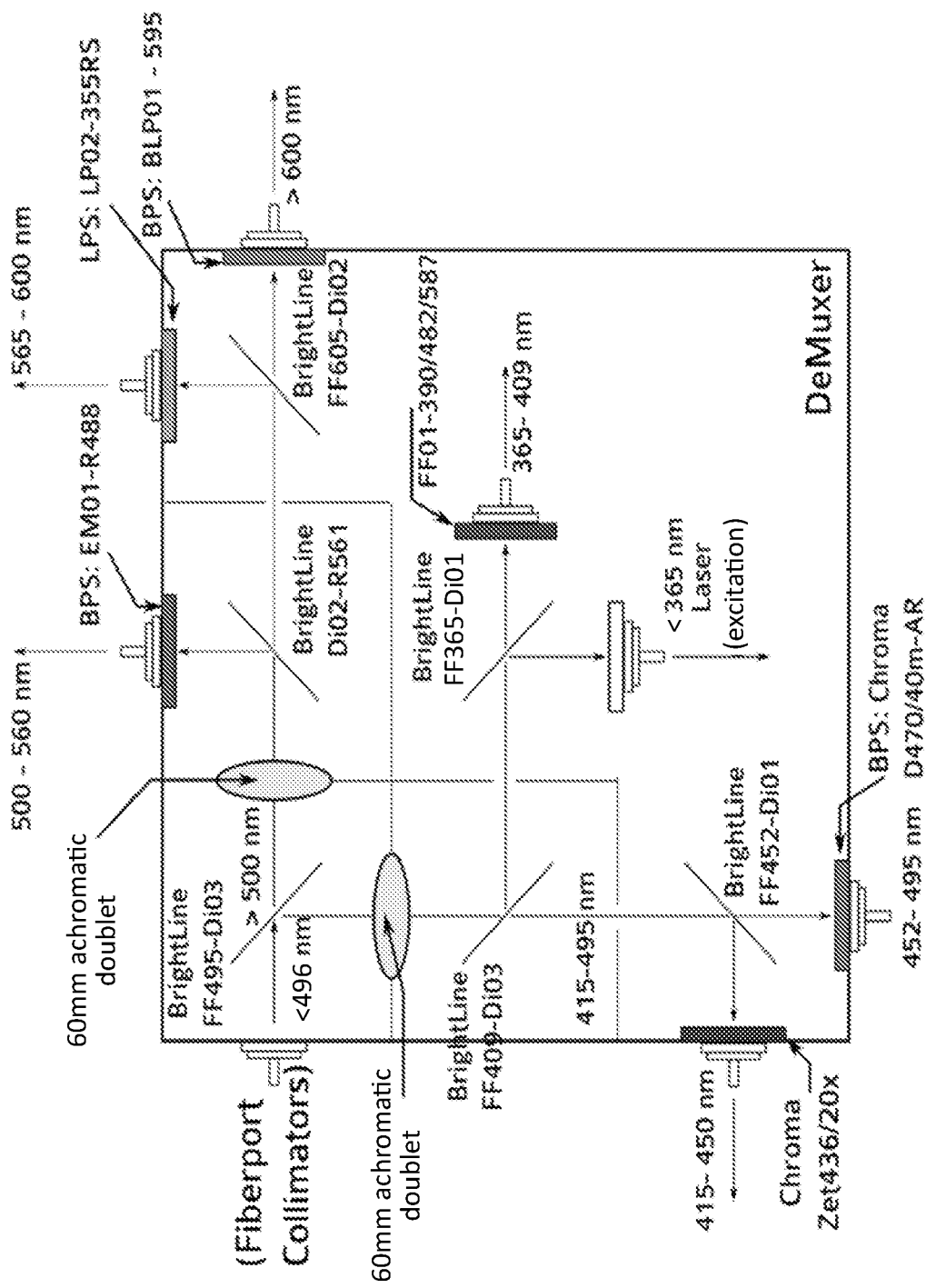
FIG. 2 depicts, in accordance with various embodiments of the present invention, a schematic of an exemplary demultiplexer design.

FIG. 2 shows schematics of wavelength splitting devices (demultiplexers, demuxers). Laser-induced light emission signal (containing a wide range of wavelengths) from the biological sample is collected by a light-collecting fiber, which brings the emitted signal towards wavelength-splitting device.

In an exemplary embodiment of the invention, the biological sample is excited at wavelengths of about 337-350 nm. In an embodiment, the wavelength splitting device (demultiplexer) depicted in FIG. 1A and FIG. 2 splits the incoming signal at wavelengths of: less than 365 nm (excitation wavelength), 365-410 nm, 410-450 nm, 450-480 nm, 500-550 nm, 550-600 nm, and greater than 600 nm. As shown in FIG. 1A, the incoming light signal is directed onto the first beam splitting device of wavelength-splitting device which splits the incoming signal at wavelengths of greater than about 495 nm and less than about 495 nm. After passing through the first beam splitting device, the signal with the wavelength of greater than 495 nm is focused using a 60 mm focal length biconcave lens and then passes through a second beam splitting device that splits the signal at wavelengths of 500-560 nm and greater than 560 nm, finally the third beam splitter splits the light in 560-600 nm and greater than 600 nm. The signal with wavelength of less than 495 nm also pass through a 60 mm focal length biconcave lens a is focused before passing via the fourth beam splitting device that splits the 495 nm light signal to wavelengths of about 410-480 nm and less than 410 nm. The light signal with the wavelength of 410-450 nm pass through a fifth beam splitting device that splits the signal to wavelengths of about 415-450 nm and 450-495 nm. The light signals from wavelength less than 410 nm goes through a sixth beam splitter and is split in wavelengths 365-410 nm and less than 365 nm wavelength, which contains the laser excitation signal. By recording the laser simultaneously with the fluorescence, it is possible to ensure accurate deconvolution. This demultiplexer design allows detection of biomolecules including but not limited to flavin mononucleotide (FMN) riboflavin, flavin adenine dinucleotide (FAD) riboflavin, lipopigments, endogenous porphyrin as well as fluorescence of molecules such as NADH and PLP-GAD in the incoming signals. Beam splitting device mentioned above can be but is not limited to a dichroic filter, prism, and diffraction grating.

In another exemplary embodiment of the invention, the biological sample is excited at wavelengths of about 337-350 nm. In this embodiment, the wavelength splitting device splits the incoming signal at wavelengths of: less than 400 nm, 415-450 nm, 455-480 nm, 400-600 nm and greater than 500 nm. Upon exiting light-collection fiber and before entering wavelength splitting device, the emitted light is first collimated using a collimating lens. Collimating lens can include, but is not limited to, a Gradient Index (GRIN) lens, or an aspheric lens. The collimated light beam is directed onto the first beam splitting device of wavelength-splitting device which splits the incoming signal at wavelengths of greater than about 400 nm and less than about 400 nm. After passing through the first beam splitting device, the signal with the wavelength of greater than 400 nm passes through a second beam splitting device that splits the signal at wavelengths of 400-500 nm and greater than 500 nm. The signal with wavelength in the range of 400-500 nm passes through a third beam splitting device that splits the light signal to wavelengths of about greater than 450 nm and less than 450 nm. In various embodiments, signal with wavelengths of less than 450 nm are analyzed for activities of biomolecules. These wavelengths are important for measuring biomolecules including but not limited to free and bound forms of NADH, PLP-GAD or combinations thereof.

By changing the configuration of beam splitting devices spectral bands of various wavelengths may be detected. Other wavelength bands can be achieved using different sets of filters which will be apparent to the person of skill in the art.

Temporal Delay Optical Device

As shown in FIG. 1A, each resolved wavelength component from the wavelength-splitting device is coupled to a corresponding delay device and subsequently undergoes a predetermined amount of delay in the corresponding delay device. In various embodiments, the delay devices are optical fibers with different lengths L1, L2, L3, L4 and so on. In a specific embodiment, the lengths of the optical fibers may be about 5 ft, 55 ft, 115 ft, 165 ft, 215 ft, 265 ft and 315 ft. Other lengths of optical fibers may be selected based on the required delay which will be apparent to the person of skill in the art. To temporally separate each of the wavelength components at the same optical detector, each of the wavelength component travels through a different length of optical fiber, and thereby experiences a different amount of delay. Eventually, each of the wavelength components arrives at the optical detector at different time which enables each component to be detected separately.

In addition to the length of the optical fiber, other physical properties of the optical fiber, including, but is not limited to, the refractive index of the fiber are also used to determine the length of the fiber to achieve a specified amount of delay. Since in the time-domain, each spectral component has a decay profile that lasts for a specific amount of time (e.g., tens of nanoseconds), the temporal delay between two adjacent spectral components can be designed to be sufficiently long to temporally separate the two decay profiles.

In one embodiment of the present invention, the optical detector is a gated MCP-MCP-PMT which only responds to incoming light signals within a short detection window controlled by a gate control circuit. This gated window can be designed to be sufficiently long so that all the resolved and temporally separated wavelength components will arrive at the MCP-PMT within the gated window. Hence, the gated MCP-PMT can capture all wavelength components which are caused by a single laser induced-emission within one detecting window. The delay device which is used to temporally separate the resolved spectral bands is not limited to optical fibers, and any delay device can generally be used.

In various embodiments, the sample is a solid, semi-solid or liquid biological sample. In various embodiments, the sample is any one or more of blood, plasma, urine, tissue, microorganisms, parasites, sputum, vomit, cerebrospinal fluid or any other biological sample from which the chemical signature can be detected.

In various embodiments, tissue can be any one or more of prostate, lung, kidney, brain, mucosa, skin, liver, GI tract, colon, bladder, muscle, breast and/or cervix.

The system described herein may be used to detect any molecule that has a detectable (for example, emitted) signature. In some embodiments, the emitted signature is a fluorescent emission. In some embodiments, the signature is fluorescence emission decay.

The demultiplexer design described herein allows detection of, for example, therapeutic agents (labeled or unlabeled), antibodies (labeled or unlabeled), toxin (labeled or unlabeled), endotoxins (labeled or unlabeled), exotoxins (labeled or unlabeled), tumor markers and/or a combination thereof. In various embodiments, unlabeled biomolecules have intrinsic fluorescence.

The system described herein allows detection of biomolecules including but not limited to flavin mononucleotide (FMN) riboflavin, flavin adenine dinucleotide (FAD) riboflavin, lipopigments, endogenous porphyrin as well as fluorescence of molecules such as NADH and PLP-GLD in the incoming signals.

In various embodiments, the therapeutic agents include chemotherapeutic agents. Examples of chemotherapeutic agents include but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof. As described herein, the chemotherapeutic agents may be labeled or unlabeled (for example, agents having intrinsic fluorescence). In some embodiments, the label is a fluorescent label. Examples of fluorescent labels that may be used with the systems, apparatus and methods described herein to label the therapeutic agents include but are not limited to indocyanine green (ICG), curcumin, rhodamine (such as rhodamine B, rhodamine 123, rhodamine 6G or variants thereof), green fluorescent protein (GFP), luciferin, fluorescein, quantum dots or a combination thereof In various embodiments, antibodies, including therapeutic antibodies include but are not limited to 3F8, 8H9, Abagovomab, Abciximab, Actoxumab, Adalimumab, Adecatumumab, Aducanumab, Afelimomab, Afutuzumab, Alacizumab pegol, ALD518, Alemtuzumab, Alirocumab, Altumomab pentetate, Arnatuximab, Anatumomab mafenatox, Anifrolumab, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansinc, Cantuzumab ravtansine, Caplacizumab, Capromab pendetide, Carlumab, Catumaxomab, cBR96-doxorubicin immunoconjugate, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxctan, Icrucumab, Igovomab, IMAB362, Imciromab, Imgatuzumab, Inclacumab, Indatuximab ravtansine, Infliximab, Inolimomab, Inotuzumab ozogamicin, Intetumumab, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodeleizumab, Lorvotuzumab mertansine, Lucatumumab, Lumiliximab, Mapatumumab, Margetuximab, Maslimomab, Matuzumab, Mavrilimumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Namatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Ontuxizumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Scribantumab, Setoxaximab, Sevirumab, SGN-CD19A, SGN-CD33A, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab (tremelimumab), Tigatuzumab Tildrakizumab, TNX-650, Tocilizumab (atlizumab), Toralizumab, Tositumomab, Tovetumab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, Zolimomab aritox. As described herein, the antibodies may be labeled or unlabeled. In some embodiments, the label is a fluorescent label. Examples of fluorescent labels that may be used with the systems, apparatus and methods described herein to label the therapeutic agents include but are not limited to indocyanine green (ICG), curcumin, rhodamine (such as rhodamine B, rhodamine 123, rhodamine 6G or variants thereof), green fluorescent protein (GFP), luciferin, fluorescein, quantum dots or a combination thereof.

In various embodiments, toxins include but are not limited to alpha toxin, anthrax toxin, bacterial toxin, diphtheria toxin, exotoxin, pertussis toxin, shiga toxin, shiga-like toxin, heat-stable enterotoxins, channel forming toxins, mycotoxins, cholera toxin, scorpion venom, cholorotoxin and/or tetanus toxins. As described herein, the toxins may be labeled or unlabeled. In some embodiments, the label is a fluorescent label. Examples of fluorescent labels that may be used with the systems, apparatus and methods described herein to label the therapeutic agents include but are not limited to indocyanine green (ICG), curcumin, rhodamine (such as rhodamine B, rhodamine 123, rhodamine 6G or variants thereof), green fluorescent protein (GFP), luciferin, fluorescein, quantum dots or a combination thereof.

In some embodiments, proteins (for example, cell surface proteins) may be detected using the system described herein. In some embodiments, the proteins may be detected using antibodies (for example, labeled or unlabeled antibodies) that bind to the cell surface markers. In some embodiments, the proteins may be detected using siRNAs (for example, labeled or unlabeled siRNAs) that bind to the proteins of interest. Examples of proteins that may be detected using the system described herein include but are not limited to 4-1BB, 5T4, adenocarcinoma antigen, alpha-fetoprotein, anncxin (for example, anncxins A1, A2, A5), BAFF, B-lymphoma cell, C242 antigen, CA-125, carbonic anhydrase 9 (CA-IX), C-MET, CCR4, CD152, CD19, CD20, CD200, CD22, CD221, CD23 (1gE receptor), CD28, CD30 (TN-FRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-1, IgG1, L1-CAM, IL-13, IL-6, insulin-like growth factor I receptor, integrin $\alpha5\beta1$, integrin $\alpha\nu\beta3$, MORAb-009, MS4A1, MUCI, mucin CanAg, N-glycolylneuraminic acid, NPC-1C, PDGF-R $\alpha$, PDL192, phosphatidylserine, prostatic carcinoma cells, RANKL, RON, ROR1, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2 or vimentin. Additional examples include but are not limited to AOC3 (VAP-1), CAM-3001, CCLII (cotaxin-1), CD125, CDI47 (basigin), CD154 (CD40L), CD2, CD20, CD23 (IgE receptor), CD25 ($\alpha$ chain of IL-2 receptor), CD3, CD4, CD5, IFN-$\alpha$, IFN-$\gamma$, IgE, 1gE Fc region, IL-1, IL-12, IL-23, IL-13, IL-17, IL-17A IL-22, IL-4, IL-5, IL-5, IL-6, IL-6 receptor, integrin $\alpha4$, integrin $\alpha4\beta7$, Lama glama, LFA-1 (CD11a), MEDI-528, myostatin, OX-40, rhuMAb $\beta7$, sclerosein, SOST, TGF beta 1, TNF-$\alpha$, VEGF-A, beta amyloid, MABT5102A, L-1$\beta$, CD3, C5, cardiac myosin, CD41 (integrin alpha-II$\beta$), fibrin II, beta chain, ITGB2 (CD18), sphingosine-1-phosphate, anthrax toxin, CCR5, CD4, clumping factor A, cytomegalovirus, cytomegalovirus glycoprotein B, endotoxin, *Escherichia coli* proteins, hepatitis B surface antigen, hepatitis B virus, HIV −1, Hsp90, Influenza A hemagglutinin, lipoteichoic acid, *Pseudomonas aeruginosa*, rabies virus glycoprotein, respiratory syncytial virus, TNF-$\alpha$, Lewis Y and CEA antigens, Tag72, folate binding protein or combinations thereof. In some embodiments, the proteins are labeled. In some embodiments, the label is a fluorescent label. Examples of fluorescent labels that may be used with the systems, apparatus and methods described herein to label the therapeutic agents include but are not limited to indocyanine green (ICG), curcumin, rhodamine (such as rhodamine B, rhodamine 123, rhodamine 6G or variants thereof), green fluorescent protein (GFP), luciferin, fluorescein, quantum dots or a combination thereof.

Methods

Figure 4:
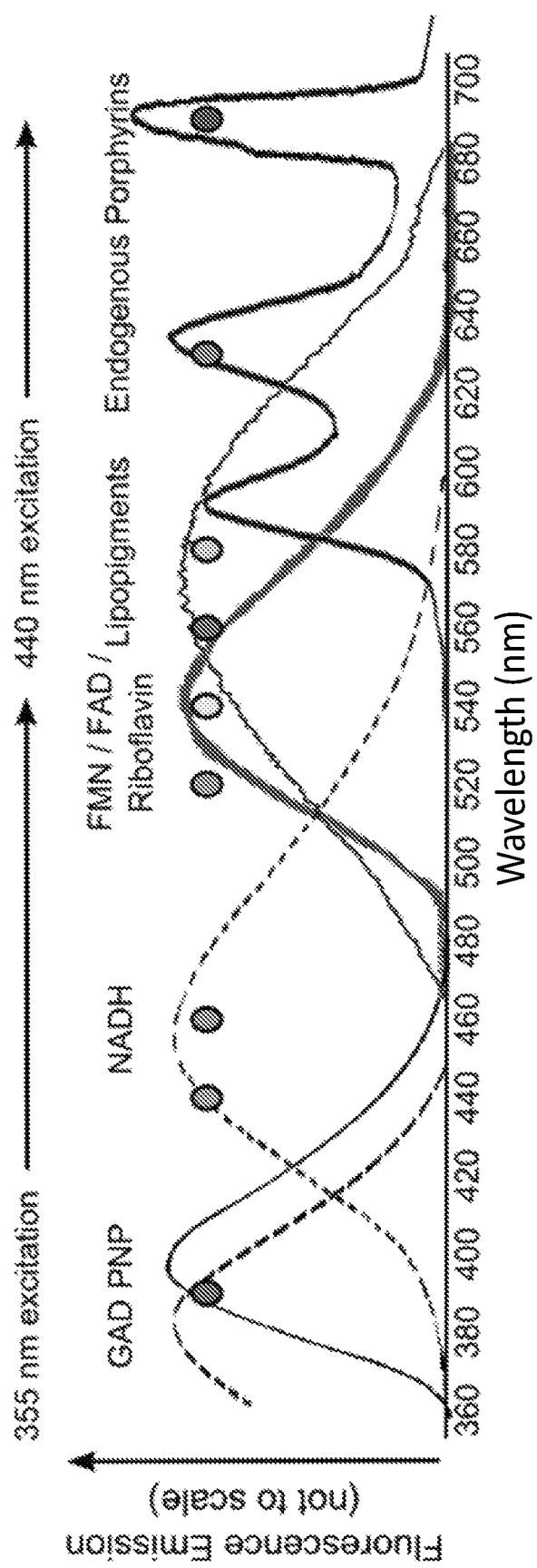
FIG. 4 depicts, in accordance with various embodiments of the present invention, fluorescence emissions of various exemplary biomolecules.

Based on the combination of the excitation wavelengths and the wavelength-splitting beam splitting devices in the demuxer, fluorescence of various molecules may be assayed (FIG. 4). For example, with excitation of the sample at wavelength of 350 nm and appropriate wavelength-splitting beam splitting devices in the demuxer, fluorescence of biomolecules including but not limited to PLG-GAD (pyridoxal-5'-phosphate (PLP) glutamic acid decarboxylase (GAD)), bound NADH and free NADH, may be assayed. Or, at an excitation of the sample at wavelength of 440 nm and appropriate wavelength-splitting beam splitting devices in the demuxer, fluorescence of biomolecules such as FAD (flavin adenine dinucleotide), FMN (flavin mononucleotide) and porphyrins can be assayed.

The invention provides methods for determining tissue viability after injury in a subject in need thereof, using the TRLIFS system described herein. The method includes using the system described herein to measure the fluorescence emitted from biomolecules (for example, NADH redox state) wherein an alteration in the fluorescence signal is indicative of tissue viability. In some embodiments, an alteration in the fluorescence signal of biomolecules is an increase in the fluorescence signal from biomolecules in the subject relative to the control (normal) subject. In some embodiments, an alteration in the fluorescence signal of biomolecules is a decrease in the fluorescence signal from biomolecules in the subject relative to the control (normal) subject. In an embodiment, an alteration in NADH redox state is indicative of tissue viability. In one embodiment, an increase in NADH fluorescence in a subject is indicative of NADH accumulation and poor tissue viability.

The invention also provides methods for monitoring cellular metabolism in a subject in need thereof, using the system described herein. The method includes using the TRLIFS system described herein to measure the fluorescence emitted from biomolecules (for example, NADH redox state) wherein an alteration in the fluorescence signal is indicative of cellular metabolism. In some embodiments, an alteration in the fluorescence signal of biomolecules is an increase in the fluorescence signal from biomolecules in the subject relative to the control (normal) subject. In some embodiments, an alteration in the fluorescence signal of biomolecules is a decrease in the fluorescence signal from biomolecules in the subject relative to the control (normal) subject. In an embodiment, NADH fluorescence may be used to monitor cellular metabolism. Cellular metabolism may be monitored continuously or periodically. In various embodiments, continuous monitoring of cellular metabolism allows, for example, assessment of viability and vulnerability of cells in ischemic condition, effects of drugs (for example, during drug development or for optimizing therapeutic windows) on cellular metabolism and/or simultaneous monitoring pH and oxygen levels to determine the metabolic state of the cell.

As described herein, the invention also provides methods for tumor detections using TRLIFS systems described herein.

EXAMPLES

Example 1

Continuous Monitoring of Cellular Metabolism

Figure 5:
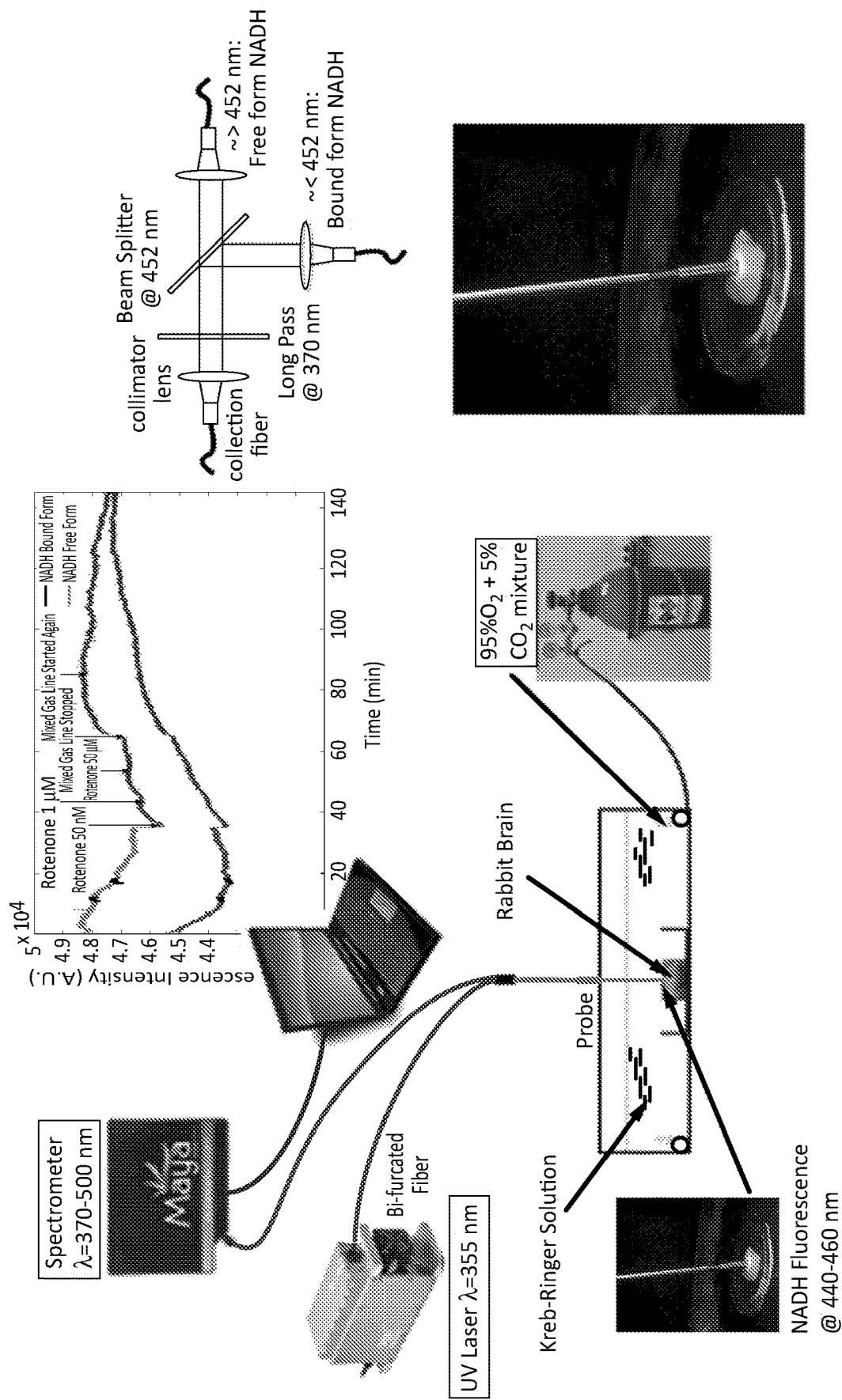
FIG. 5 depicts, in accordance with various embodiments of the present invention, a schematic showing the use of continuous NADH monitoring in an ex-vivo brain sample.

The systems described herein allow continuous monitoring of the changes in the NADH level at very minute scales to determine changes in metabolic status in response to oxygen depletion, effect of neuro-protective drugs etc. (FIG. 1A and FIG. 5).

Nicotinamide adenosine dinucleotide (NADH) is involved in redox reaction for ATP production in aerobic respiration. NADH is produced in mitochondrion during glycolysis and citric acid (TCA) cycle. NADH is oxidized to NAD+ at the mitochondrial membrane producing ATP in the process. This process is disrupted in conditions including but not limited to ischemia due to stroke. In a low oxygen condition, NADH accumulates in the cell, and persistent oxygen depletion may result in cell death, leading to complete breakdown of NADH. These variations in NADH level allow assessment of viability and vulnerability of cells in ischemic condition. Fluctuations in NADH levels may be evaluated by measuring the fluorescence emission from NADH. NAD+ and NADH both have a strong absorption in UV spectrum, but they differ in their fluorescence characteristics. NADH demonstrates strong fluorescence in the violet/blue band around 440/460 nm of wavelength depending of its bound (to cytochrome) versus free state. Measuring this fluorescence in real time allows monitoring of changes in the NADH level, assessing the metabolic status of NADH, thereby monitoring cellular metabolism.

In order to excite the tissue, a Q-switched Nd:YaG laser emitting at a wavelength of 350 nm was used, running at 1 KHz with a pulse width (FWHM) of 400 ps (Teem Photonics PNVM02510). Total energy per pulse did not exceed 50 µJ which prevented photo-bleaching of NADH. The excitation light was delivered to the tissue using a custom made trifurcated optical probe. The probe consisted of a central 600 micron fiber for delivering the excitation light surrounded by twelve 200 micron fibers to collect the fluorescence (FIG. 3). Every other fiber from the twelve collection fibers were bundled together forming two channels. One collection channel/bundle connected to a spectrometer (Ocean Optics, Maya), which measured the fluorescence spectrum every 100 ms and the other channel/bundle connected to a beam splitter (demultiplexer). The beam splitter at 452 nm of wavelength separated the significant free and bound fluorescence, which was recorded both by MCP-PMT and spectrometer.

Rabbit brain was removed after sacrificing the animal in the OR and transported in cold oxygen rich Kreb-ringer solution to the laboratory. The cortex was separated and placed in Kreb-Ringer solution with continuous bubbling of the 95% $O_2$ and 5% $CO_2$ mixture to keep the tissue alive. The probe was adjusted on the tissue in order to record the fluorescence as shown in FIG. 5. A baseline NADH (bound and free) was recorded till the fluorescence from the tissue equilibrated and plateaued. After approximately 30 mins, a measured dose of 50 nM rotenone, which blocks the binding of NADH to cytochrome in the mitochondrion, was added. Additional concentrations of rotenone were added every 10 mins.

Figure 6:
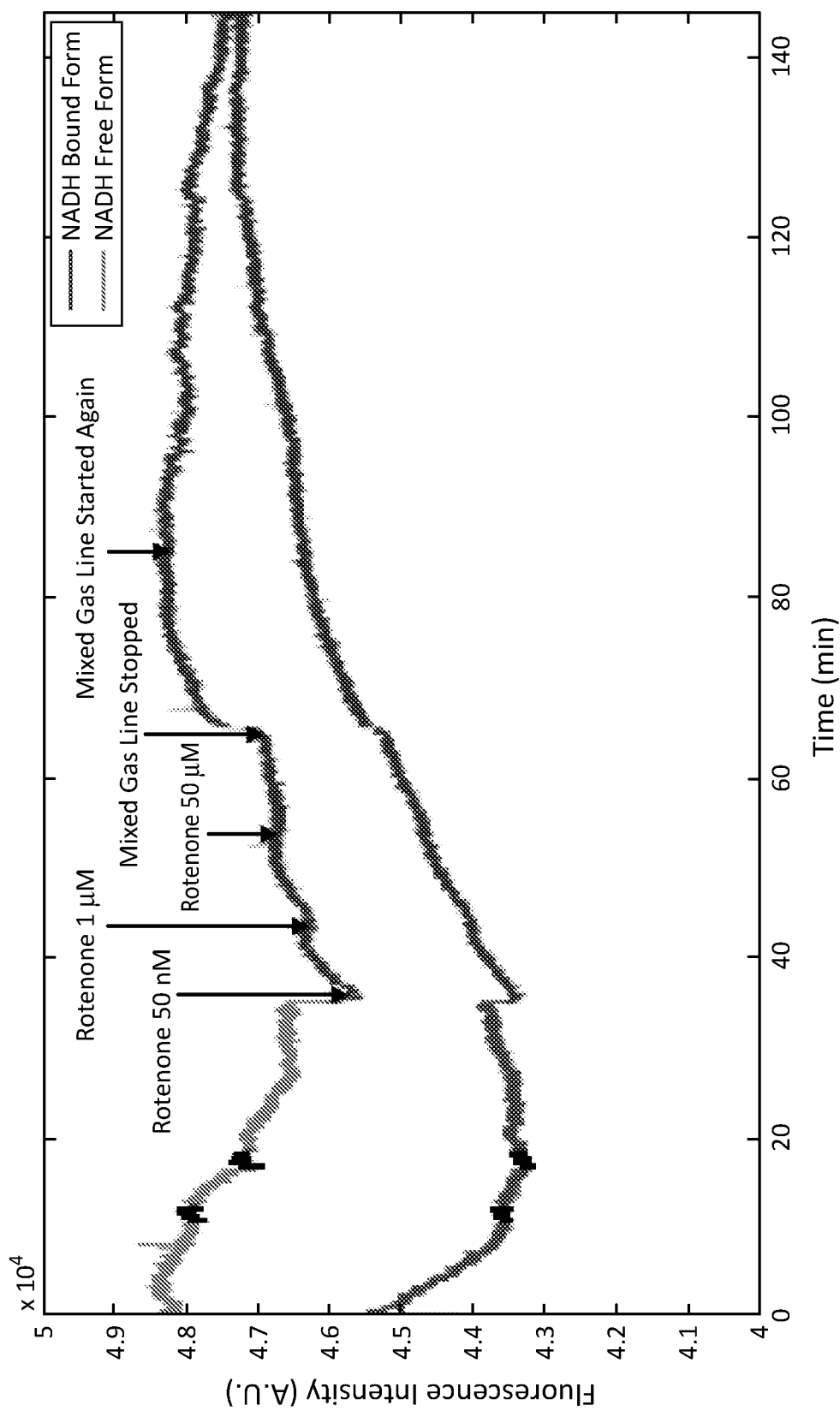
FIG. 6 depicts, in accordance with various embodiments of the present invention, data demonstrating capabilities of the TRLIFS apparatus to continuously monitor the NADH level while the cells are exposed to Rotenone, a compound which interferes with NADH-dependent ATP production.

The effect of various concentrations of Rotenone on the rabbit brain tissue was recorded (FIG. 6). The results showed that the concentrations of both free and bound NADH can be mapped in real-time (every ~100 ms) and response to the external stimuli was recorded. FIG. 6 shows a continuous plot of NADH fluorescence level over a period of more than 2 hours. On adding the 50 nM concentration of Rotenone to the solution, an increase in NADH level was observed as expected due to blocking on NADH consumption and subsequent accumulation. As the concentration of Rotenone increased the NADH fluorescence increased as expected. At 80 mins time, the gas which was continuously bubbling through the liquid was stopped and then restarted allowing assessment of the effect of hypoxia on accumulation of NADH in the tissue and its subsequent consumption once the oxygen supply was restored. This demonstrated the ability of TRLIFS system described herein to monitor the metabolic state in realtime.

Example 2

Determining Tissue Viability After Injury

Recording the NADH levels over a large area of brain after an ischemic stroke permits assessment of the number of viable cells that may be in shock due to lack of oxygen, but may not have undergone apoptosis and thus are salvageable. These cell form the bulk of the region known as the penumbra and an important goal of stroke treatment is to reduce the size of penumbra while salvaging as many neurons as possible. Monitoring NADH over the entire penumbra region allows assessment of the effectiveness of various interventions designed for the same.

In order to excite the tissue, a Q-switched Nd:YaG laser emitting at a wavelength 350 nm was used, running at 1 KHz with a pulse width (FWHM) of 400 ps (Teem Photonics PNVM02510). Total energy per pulse did not exceed 50 µJ which prevented photo-bleaching of NADH. The excitation light was delivered to the tissue using a custom made trifurcated optical probe. The probe consisted of a central 600 micron fiber for delivering the excitation light surrounded by twelve 200 micron fibers to collect the fluorescence. Every other fiber from the twelve collection fibers were bundled together forming two channels. One collection channel/bundle connected to a spectrometer (Ocean Optics, Maya), which measured the fluorescence spectrum every 100 ms and the other channel/bundle connected to a beam splitter (demultiplexer).

Figure 7A:
FIG. 7A depicts the areas observed by the TRLIFS system.

A rabbit brain stroke model was used in which a stroke was caused in the rabbit brain by injecting a clot in the cerebral artery. The rabbit was sacrificed after testing for neurological damage. The brain was removed and transported to the laboratory in cold $O_2$ saturated Kreb-Ringer Solution. In the laboratory, the infarcted cortex was separated from rest of the brain and placed in the Kreb-Ringer solution with bubbling 95% $O_2$ and 5% $CO_2$ mixture. A single reading was recorded from the edge of the cortex and the probe was moved over the surface of the cortex as shown in FIG. 7A. The fluorescence intensity was recorded from the tissue sample. The tissue sample was submerged in the solution of TTC (2,3,5-triphenyl tetrazolium) which when taken up by the viable cells turns the cell red. TTC is currently a gold standard for testing the viability of cells. TTC stained tissue was compared to the recorded fluorescence intensity.

Figure 7B:
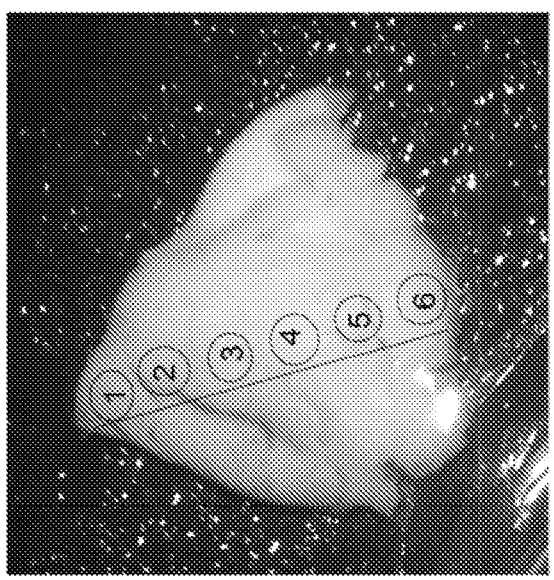
FIG. 7B depicts the sample from FIG. 7A is overlapped after treatment with TTC.
Figure 7C:
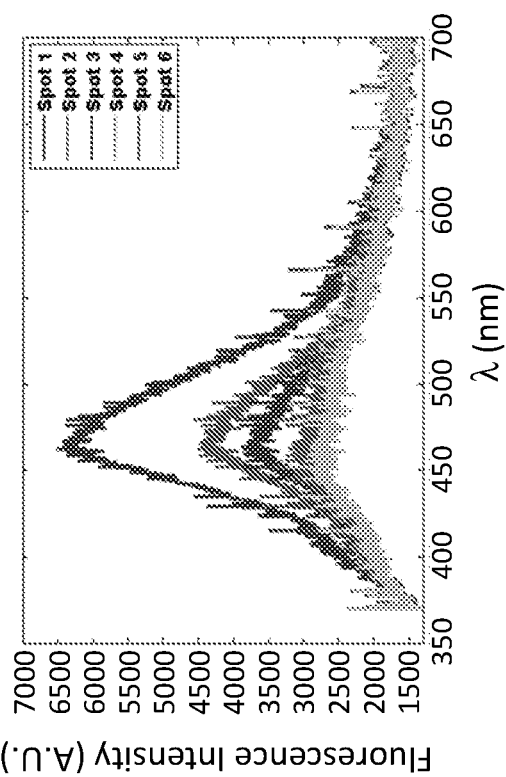
FIG. 7C depicts the fluorescence intensity plotted for each area (spot).

A smooth gradient in NADH auto-fluorescence from healthy tissue (red stained area in FIG. 7B) to the dead tissue (unstained area in FIG. 7B) was observed. We also noted that instead of an abrupt change from the viable to dead brain tissue as seen with TTC staining the fluorescence intensity (FIG. 7C) changed gradually, indicating presence of viable cells in the region indicated as dead.

Example 3

Use of Fluorescence to Determine the Level of Drug/Metabolite in Plasma

Figure 8:
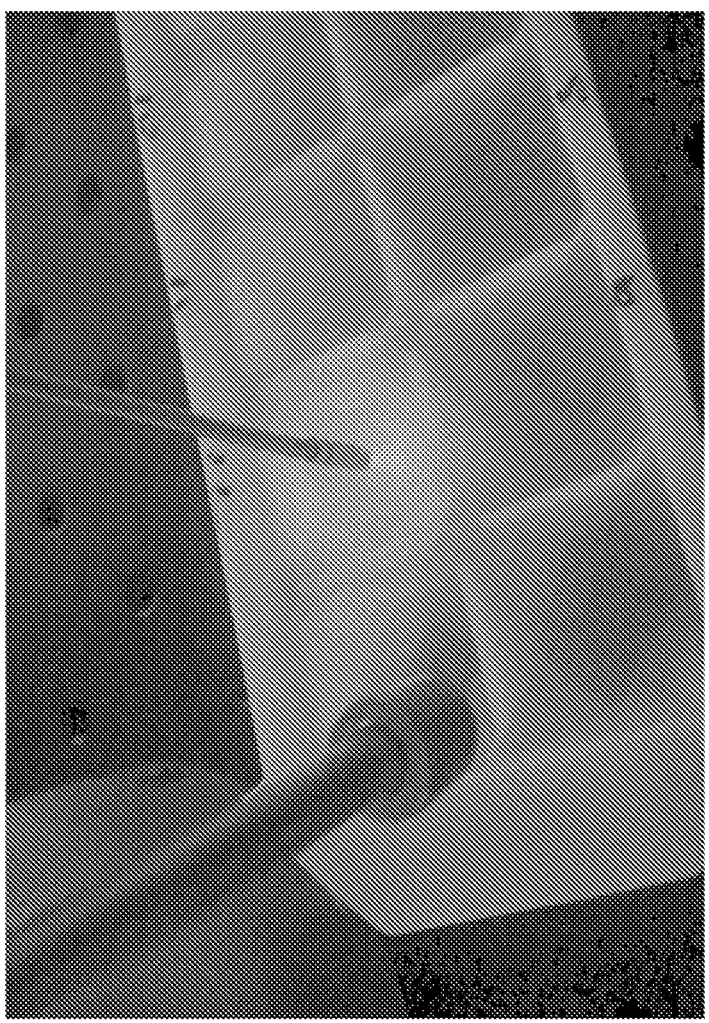
FIG. 8 depicts, in accordance with various embodiments of the present invention, agar/gel with varying concentrations of methotrexate.

Some anticancer drugs are toxic at high dosages and lose their efficacy at lower dosages. This optimal plasma concentration of the drug at which the drug is most effective (therapeutic window) varies amongst patients due to variation in height, weight, metabolism and ethnicity. In spite of these variations, currently the drug dosages are calculated based on the weight of the patient and a standardized pharmacokinetic profile. A quick and inexpensive method to determine the plasma drug level allows optimization of dosages for individual patients. The plasma level of drugs may be detected using fluorescence spectroscopy. It is known that some of the anticancer drugs such as methotrexate have fluorescent properties. Herein Applicants show that using the TRLIFS systems described herein, varying the concentrations of methotrexate (MTX) in agar (FIG. 8) resulted in corresponding change in fluorescence of MTX.

In order to excite the agar gel, a Q-switched Nd:YaG laser emitting at wavelength of 350 nm was used, running at 1 KHz with a pulse width (FWHM) of 400 ps (Teem Photonics PNVM02510). Total energy per pulse did not exceed 50 µJ which prevents photo-bleaching of NADH. The excitation light was delivered to the gel using a custom made trifurcated optical probe. The probe consisted of a central 600 micron fiber for delivering the excitation light surrounded by twelve 200 micron fibers to collect the fluorescence. Every other fiber from the twelve collection fibers were bundled together forming two channels. One collection channel/bundle goes to a spectrometer (Ocean Optics, Maya), which measure the fluorescence spectrum every 100 ms and the other channel/bundle connected to a beam splitter (demultiplexer).

Figure 9A:
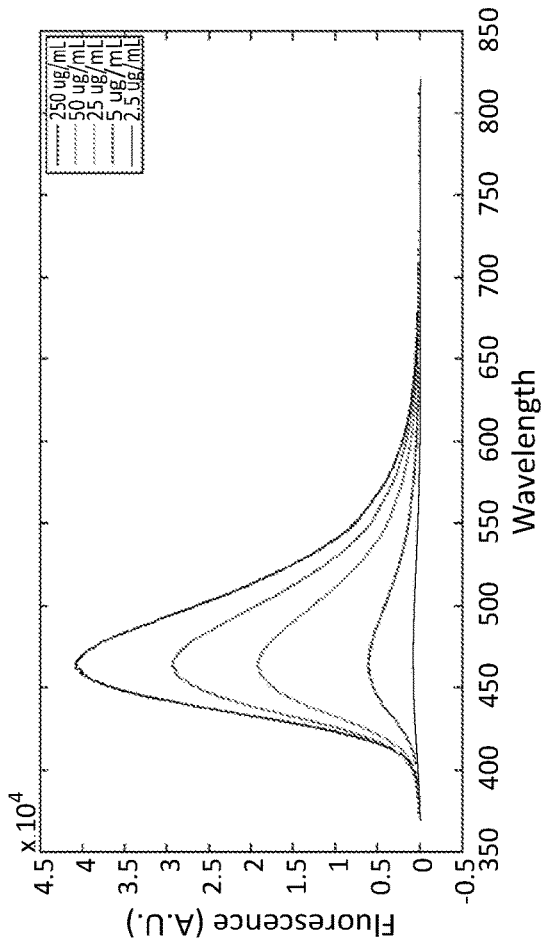
FIG. 9A depicts fluorescence of MTX at varying concentrations after 20 mins exposure to light with wavelength of 350 nm.
Figure 9C:
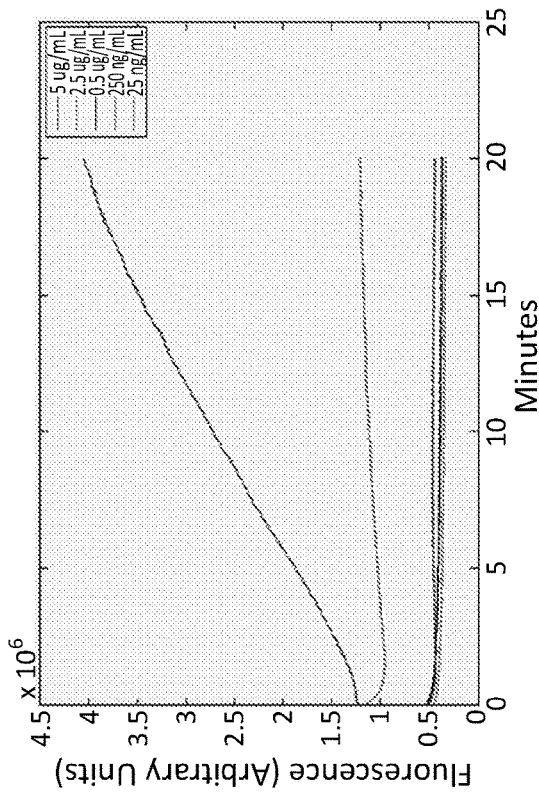
FIGS. 9B-9C depict plots of the fluorescence time course over 20 mins indicating increase in the fluorescence of MTX due to formation of active fluorescent form.
Figure 9B:
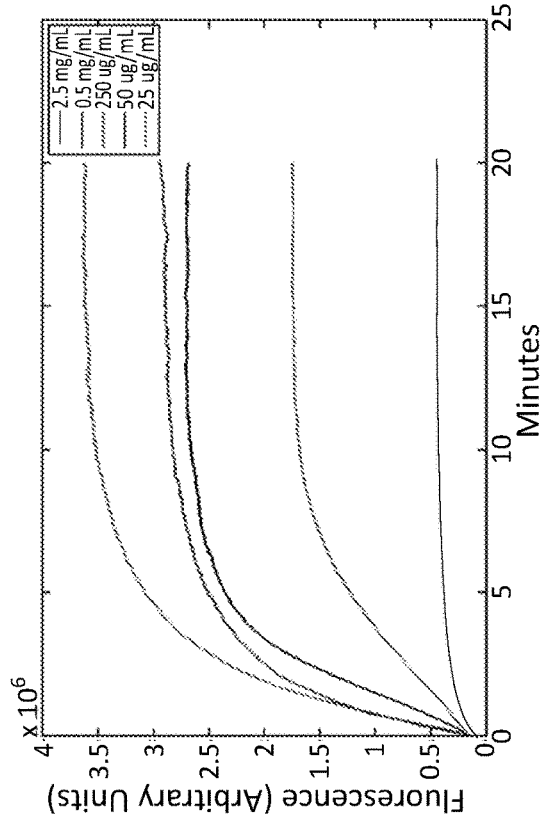

A serial dilution of MTX (25 µg/ml to 25 ng/ml) was prepared in agar gel. MTX when exposed to UV light is converted to a more fluorescent form. Upon exposure to UV light the fluorescent form accumulates. In order to detect the fluorescent form the conversion from low fluorescence to fluorescent form was allowed to take place until a saturation level was reached. The final fluorescence intensity was recorded and compared to the concentration. The fluorescence intensity of MTX after 20 mins of UV light exposure is a good indicator of the concentration of MTX in the agar gel as shown in FIGS. 9A-9C.

Example 4

Tumor Detection

Laser-induced fluorescence spectroscopy (LIFS) represents a promising new adjunctive technique for in vivo diagnosis. Fluorescence spectroscopy involves exciting the endogenous fluorophores (label-free) within tissues and recording the emission. Fluorescence spectroscopy can by employed in two ways, steady-state or time-resolved fluorescence spectroscopy. The time-resolved measurement resolves fluorescence intensity decay in terms of lifetimes and thus provides additional information about the underlying dynamics of the fluorescence intensity decay. Time-resolved measurements are also independent of factors such as absorption by tissue endogenous fluorophores (e.g blood), photobleaching or any other condition that may affect the fluorescence intensity. By measuring the fluorescence decay characteristics, which reflect the differences in the relaxation dynamics of distinct fluorescent molecules, time-resolved measurements have an ability to resolve overlapping spectra, and improve the specificity of the fluorescence measurement.

Applicants show that in patients, the TR-LIFS systems described herein can discriminate glioma tumors (both high- and low-grade) from the surrounding normal brain tissue intra-operatively. This work is to establish the TR-LIFS potential to enhance the ability of the neurosurgeon-neuropathologist team to rapidly distinguish between tumor and normal brain during surgery.

Instrumentation: Experiments were conducted with an instrument setup, which allowed for spectrally-resolved fluorescence lifetime measurements. A schematic of the optical and electronic layout of the apparatus is shown in FIG. 1A. Briefly, it consisted of a) A pulsed Q-switch Nd:YaG laser (Teem Photonics, model Teem Photonics PNVM02510, λ=350 nm, pulse width=400 ps FWHM, pulse rate=1 KHz) which was used as the excitation source, b) a custom made sterilizable trifurcated fiber-optic probe (Fiberguide, N.J.), c) a gated multi-channel plate photo-multiplier tube (MCP-PMT Photek, UK, model 210, rise time=80 ps) with an optional fast preamplifier (Photek, UK, model PA200-10, 2 GHz), e) a digitizer (ADQ-108, SPDevices, Sveden, 7 Gsamples/sec), and f) a computer Laptop, g) a custom made demuxer as shown in FIG. 1A and peripheral electronics. The instrument allowed for mobility as it was contained in a standard endoscopic cart (70×70×150 cm3) internally modified to accommodate the individual devices. To ensure a very low noise level from the electronics used such as a high voltage supply and preamplifier power supply, all the instruments are shielded from the main power supply using a medical grade Isolation transformer (Toroid® ISB-170A).

Delivery catheter: Light delivery and collection were implemented with a custom made bifurcated sterilizable probe. The probe consisted of non-solarizing silica/silica step index fibers of 0.11 numerical aperture (NA) (Fiberguide, New Jersey, N.J.). It had a central excitation fiber of 600 µm core diameter, surrounded by a collection ring of twelve 200 µm core diameter fibers. All the collection fibers were bundled together and combined into a single 600 micron fiber. The center-to-center separation between the excitation and collection fibers was 480 µm. The probe was flexible throughout its entire length (3 meters) except of a 7 cm distal part consisted of a rigid stainless steel tube. This facilitated the mounting and micromanipulation of the probe. A spacer with two slits on the opposite sides was added in front of the distal end of the probe. This allowed the probe to be in contact with the tissue while maintaining a fixed distance from the tissue. The two slits on the spacer enabled the surgeon to apply a suction tube to maintain a clear field. The laser light was coupled into the illumination channel of the probe with a standard SMA connector, while the distal end of the collection channel was formed into a straight line in order to facilitate coupling to the spectrograph. After tissue excitation, the emitted fluorescence light was collected and directed into the entrance slit of the demuxer by bundle one and spectrometer via bundle two. The signal was then detected by the MCP-PMT, amplified by the fast preamplifier, and finally digitized at 8 bits resolution by the digital oscilloscope. The overall time resolution of the systems was approximately 150 ps.

The fiber optic probe was positioned at 3 mm above the exposed brain tissue specimen with the help of a spacer to optimize the probe light collection efficiency as previously reported and to steady the probe over the tissue. Time-resolved emission of each sample was recorded at seven separate wavelength bands (355 (<365 nm)), 365-410 nm, 415-450 nm, 450-490 nm, 500-560 nm, 560-600 nm and >600 nm) spectral range. The energy output of the laser (at the tip of the fiber) for sample excitation was adjusted to 5.00/pulse. After the spectroscopic analysis the tissue was biopsied at the exact site and sent for pathological investigation.

Each biopsy sample was fixed in 10% buffered formalin. The tissue samples were fixed on the slides and stained with H&E. All biopsy specimens were studied by the pathologist and correlated with original fluorescence spectroscopy measurements results. Histologically, gliomas were categorized in low grade: Oligodendroglioma, oligodendroastrocytoma, diffuse astrocytoma (WHO Grade II), intermediate grade: anaplastic astrocytoma (WHO Grade III) and high grade: anaplastic oligodendroglioma, anaplastic oligoastrocytoma and glioblastoma multiforme (grade III-IV) based on the WHO grading. For the purpose of spectroscopic classification in this study the gliomas were grouped as low grade glioma (LGG) (grade I & II) and high grade glioma (HGG) (grade III & IV).

TR-LIFS Data Analysis: In the context of TR-LIFS, the intrinsic fluorescence impulse response functions (IRF), h(n), describes the real dynamics of the fluorescence decay. The IRF were recovered by numerical deconvolution of the measured input laser pulse from the measured fluorescence response transients. The Laguerre expansion technique was used for deconvolution. Laguerre expansion technique was selected over the more conventional multi-exponential curve fitting for a set of reasons. It allows for faster deconvolution of the fluorescence IR. Since the Laguerre basis is orthonormal, it provides a unique and complete expansion of the decay function. This technique in also non-parametric thus does not require a priory assumption of the functional form of the decay. Consequently, this allows for the approximation of fluorescence systems with unknown and complex relaxation dynamics such as that of biological tissues. This method allows a direct recovery of the intrinsic properties of a dynamic system from the experimental input-output data. The technique uses the orthonormal Laguerre functions to expand the IRF and to estimate the Laguerre expansion coefficients (LEC). The normalized fluorescence spectra were obtained by dividing the discrete intensities values with the intensity value at the peak emission. Further, to characterize the temporal dynamics of the fluorescence decay, two sets of parameters were used: 1) the average lifetime ($\tau_\lambda$) computed as the interpolated time at which the IRF decays to of its maximum value; and 2) the normalized value of the corresponding LECs. Thus, a complete description of fluorescence from each sample as a function of emission wavelength, $\lambda_E$, was given by the variation of a set of spectroscopic parameters at distinct wavelengths (emission intensity—$I_\lambda$, average lifetime of fluorescence emission—$\tau_{f\lambda}$, and Laguerre coefficients $LEC_{f\lambda}$). This analytical approach for characterization of fluorescence decay was recently developed by our research group and described in detail elsewhere. Applicants were able to recover the lifetime and Laguerre coefficient values.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

Butte, P. V, Fang, Q., Jo, J. A., Yong, W. H., Pikul, B. K., Black, K. L., & Marcu, L. (n.d.). Intraoperative delineation of primary brain tumors using time-resolved fluorescence spectroscopy. *Journal of Biomedical Optics*, 15(2), 027008. doi:10.1117/1.3374049

Butte, P. V, Pikul, B. K., Hever, A., Yong, W. H., Black, K. L., & Marcu, L. (2005). Diagnosis of meningioma by time-resolved fluorescence spectroscopy. *Journal of Biomedical Optics*, 10(6), 064026. doi:10.1117/1.2141624

Butte, P. V., Mamelak, A. N., Nuno, M., Bannykh, S. I., Black, K. L., & Marcu, L. (2010). Fluorescence lifetime spectroscopy for guided therapy of brain tumors. *NeuroImage*, 54, S125 5135. doi:10.1016/j.neuroimage.2010.11.001

Marcu, L., Jo, J. a, Butte, P. V, Yong, W. H., Pikul, B. K., Black, K. L., & Thompson, R. C. (2004). Fluorescence lifetime spectroscopy of glioblastoma multi forme. *Photochemistry and Photobiology*, 80, 98-103. doi:10.1562/2003-12-09-RA-023.1

Yong, W. H., Butte, P. V, Pikul, B. K., Jo, J. A., Fang, Q., Papaioannou, T., . . . Marcu, L. (2006). Distinction of brain tissue, low grade and high grade glioma with time-resolved fluorescence spectroscopy. *Frontiers in Bioscience: A Journal and Virtual Library*, 11(4), 1255-63. Retrieved from http://www.ncbi.nlm.nih.gov/pubmed/16368511

Jo, J. a, Fang, Q., Papaioannou, T., & Marcu, L. (2004). Fast model-free deconvolution of fluorescence decay for analysis of biological systems. *Journal of Biomedical Optics*, 9(4), 743 52. doi:10.1117/1.1752919

Lakowicz, J. R. (2006). *Principles of fluorescence spectroscopy* (3rd ed., p. xxvi, 954 p.). New York: Springer. Retrieved from http://www.loc.gov/catdir/enhancements/fy0824/2006920796-b.html Pogue, B. W., Pitts, J. D., Mycek, M. a, Sloboda, R. D., Wilmot, C. M., Brandsema, J. F., & O'Hara, J. a. (2001). In vivo NADH fluorescence monitoring as an assay for cellular damage in photodynamic therapy. *Photochemistry and Photobiology*, 74(6), 817-24. Retrieved from http://www.ncbi.nlm.nih.gov/pubmed/11783938

Schneckenburger, H. (1992). Fluorescence decay kinetics and imaging of NAD(P)H and flavins as metabolic indicators. *Optical Engineering*, 31(7), 1447. doi:10.1117/12.57704

Sun, Y., Phipps, J., Elson, D. S., Stoy, H., Tinling, S., Meier, J., Marcu, L. (2009). Fluorescence lifetime imaging microscopy: in vivo application to diagnosis of oral carcinoma. *Opt Lett*, 34(13), 2081-2083. doi:183277 [pii]

The invention claimed is:

1. A system for characterizing a biological sample by analyzing emission of fluorescent light from the biological sample upon excitation comprising:
   (a) a laser source connected to a biological sample via excitation fibers (ExF), wherein the laser is configured to irradiate the biological sample with a laser pulse at a predetermined wavelength to cause the biological sample to produce a responsive fluorescence signal;
   (b) a light collector, wherein the light collector collects the responsive fluorescence signal from the biological sample, and relays the fluorescence signal to a plurality of filters; and
   (c) the plurality of filters, each filter of the plurality of filters being configured to split the responsive fluorescence signal at pre-determined wavelengths to obtain spectral bands,
   wherein a first spectral band comprises wavelengths within a range of 410-450 nm, a second spectral band comprises wavelengths within a range of 450-480 nm, and a third spectral band comprises wavelengths within a range of 500-560 nm.

2. The system of claim 1, wherein a fourth spectral band comprises wavelengths within a range of 365-410 nm and wherein a fifth spectral band comprises wavelengths greater than 600 nm, and optionally wherein a sixth spectral band comprises wavelengths of less than 365 nm.

3. The system of claim 1, further comprising an optical delay device.

4. The system of claim 3, wherein the optical delay device is adapted to couple the spectral bands from the plurality of filters into the optical delay device, allow the spectral bands to travel through the optical delay device, and introduce a controlled time delay to the spectral bands as the spectral bands travel through the optical delay device.

5. The system of claim 3, wherein the optical delay device comprises a plurality of optical fibers and optionally wherein two or more of the plurality of optical fibers have different optical path lengths.

6. The system of claim 1, wherein the plurality of filters form a demultiplexer.

7. The system of claim 1, wherein the light collector comprises one or more collection fibers (CF) or lenses.

8. A method for characterizing a biological sample by analyzing emission of a fluorescence signal from the biological sample upon excitation comprising:
   (a) irradiating the biological sample with a laser pulse at a predetermined wavelength to cause the biological sample to produce a responsive fluorescence signal;
   (b) collecting the responsive fluorescence signal from the biological sample; and
   (c) splitting the responsive fluorescence signal with a plurality of filters, each filter of the plurality of filters being configured to split the responsive fluorescence signal at pre-determined wavelengths to obtain spectral bands,
   wherein a first spectral band comprises wavelengths within a range of 410-450 nm, a second spectral band comprises wavelengths within a range of 450-480 nm, and a third spectral band comprises wavelengths within a range of 500-560 nm.

9. The method of claim 8, wherein a fourth spectral band comprises wavelengths within a range of 365-410 nm and wherein a fifth spectral band comprises wavelengths greater than 600 nm, and optionally wherein a sixth spectral band comprises wavelengths of less than 365 nm.

10. The method of claim 8, wherein the responsive fluorescence signal is emitted by a biomolecule and optionally wherein the biomolecule is any one or more of PLP-GAD (pyridoxal-5'-phosphate (PLP) glutamic acid decarboxylase (GAD)), bound NADH, free NADH, flavin mononucleotide (FMN) riboflavin, flavin adenine dinucleotide (FAD) riboflavin, lipopigments, endogenous porphyrins or a combination thereof.

11. A method for determining tissue viability comprising analyzing emission of responsive fluorescence signals from biomolecules in the tissue by the method of claim 8, wherein an increase in responsive fluorescence signals of the biomolecule in the biological sample relative to a normal sample is indicative of poor tissue viability.

12. A method for continuously monitoring cellular metabolism comprising analyzing emission of a responsive fluorescence signal by the method of claim 8.

13. A method for determining drug or metabolite level in plasma comprising analyzing emission of a responsive fluorescence signal from a biomolecule by the method of claim 8.

14. The method of claim 8, further comprising (d) passing the spectral bands through a time-delay mechanism; (e) obtaining the time-delayed spectral bands; and (f) processing the time-delayed spectral bands.

15. The method of claim 14, wherein processing the time-delayed spectral bands comprises detecting the time-delayed spectral bands.

\* \* \* \* \*